(12) United States Patent
Koda et al.

(10) Patent No.: US 11,554,202 B2
(45) Date of Patent: Jan. 17, 2023

(54) BLOOD PURIFICATION APPARATUS AND METHOD OF DISCHARGING BUBBLES THEREFROM

(71) Applicant: Nikkiso Company Limited, Tokyo (JP)

(72) Inventors: Shunichi Koda, Shizuoka (JP); Shunsuke Kawamura, Shizuoka (JP); Shingo Okamoto, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 410 days.

(21) Appl. No.: 16/811,046

(22) Filed: Mar. 6, 2020

(65) Prior Publication Data

US 2020/0206407 A1 Jul. 2, 2020

Related U.S. Application Data

(63) Continuation of application No. PCT/JP2018/033152, filed on Sep. 7, 2018.

(30) Foreign Application Priority Data

Sep. 7, 2017 (JP) .............................. JP2017-172562

(51) Int. Cl.
*A61M 1/36* (2006.01)
*A61M 60/279* (2021.01)
(Continued)

(52) U.S. Cl.
CPC ........ *A61M 1/3653* (2013.01); *A61M 1/3607* (2014.02); *A61M 1/3638* (2014.02);
(Continued)

(58) Field of Classification Search
None
See application file for complete search history.

(56) References Cited

U.S. PATENT DOCUMENTS

| | | | |
|---|---|---|---|
| 3,046,788 A | 7/1962 | Laimins | |
| 4,090,404 A | 5/1978 | Dupont et al. | |

(Continued)

FOREIGN PATENT DOCUMENTS

| | | |
|---|---|---|
| CN | 1405450 A | 3/2003 |
| EP | 1666078 A2 | 6/2006 |

(Continued)

OTHER PUBLICATIONS

European Search Report for Application No. 18853126.3, dated May 6, 2021.

(Continued)

*Primary Examiner* — Jonathan M Peo
(74) *Attorney, Agent, or Firm* — Young Basile Hanlon & MacFarlane, P.C.

(57) ABSTRACT

Microbubbles detached from a blood circuit and a blood purification unit are discharged with the use of a backflow generated at the instant that a roller of a blood pump releases a squeezable tube. In a normal rotation step, a region filled with a priming solution after a priming step is closed by a closing unit, and a rotor of a blood pump is rotated normally until a roller of the blood pump releases a squeezable tube to generate a backflow. After the backflow is generated at the release of the squeezable tube by the roller of the blood pump, bubbles are moved by reversely rotating the rotor while disabling the closing by the closing unit. Thus, the bubbles are discharged through a discharge unit.

19 Claims, 17 Drawing Sheets

(51) Int. Cl.
  *A61M 60/833* (2021.01)
  *A61M 1/00* (2006.01)
  *A61M 60/851* (2021.01)
  *A61M 60/531* (2021.01)
  *A61M 60/554* (2021.01)
  *A61M 60/441* (2021.01)
  *A61M 60/37* (2021.01)
  *A61M 60/113* (2021.01)

(52) U.S. Cl.
  CPC ............ *A61M 1/3643* (2013.01); *A61M 1/85* (2021.05); *A61M 60/113* (2021.01); *A61M 60/279* (2021.01); *A61M 60/37* (2021.01); *A61M 60/441* (2021.01); *A61M 60/531* (2021.01); *A61M 60/554* (2021.01); *A61M 60/833* (2021.01); *A61M 60/851* (2021.01)

(56) References Cited

U.S. PATENT DOCUMENTS

| | | | |
|---|---|---|---|
| 4,460,355 | A | 7/1984 | Layman |
| 4,498,843 | A | 2/1985 | Schneider et al. |
| 4,534,756 | A | 8/1985 | Nelson |
| 4,558,996 | A | 12/1985 | Becker |
| 4,585,399 | A | 4/1986 | Baier |
| 4,743,228 | A | 5/1988 | Butterfield |
| 4,762,518 | A | 8/1988 | Kreinick |
| 4,784,576 | A | 11/1988 | Bloom et al. |
| 4,969,808 | A | 11/1990 | Tsukada |
| 5,024,099 | A | 6/1991 | Lee |
| 5,215,450 | A | 6/1993 | Tamari |
| 5,336,051 | A | 8/1994 | Tamari |
| 5,356,378 | A | 10/1994 | Doan |
| 5,380,172 | A | 1/1995 | Ulbing |
| 5,429,483 | A | 7/1995 | Tamari |
| 5,501,665 | A | 3/1996 | Jhuboo et al. |
| 5,577,891 | A | 11/1996 | Loughnane et al. |
| 5,720,721 | A | 2/1998 | Dumas et al. |
| 5,813,842 | A | 9/1998 | Tamari |
| 5,814,004 | A | 9/1998 | Tamari |
| 5,827,223 | A | 10/1998 | Butterfield |
| 5,920,054 | A | 7/1999 | Uber, III |
| 5,927,951 | A | 7/1999 | Tamari |
| 6,039,078 | A | 3/2000 | Tamari |
| 6,374,084 | B1 | 4/2002 | Fok |
| 6,423,029 | B1 | 7/2002 | Elsberry |
| 6,497,680 | B1 | 12/2002 | Holst et al. |
| 6,868,720 | B2 | 3/2005 | Lobdell et al. |
| 7,004,924 | B1 | 2/2006 | Brugger et al. |
| 7,037,092 | B2 | 5/2006 | Kagawa et al. |
| 7,462,163 | B2 | 12/2008 | Yap et al. |
| 7,935,912 | B2 | 5/2011 | Arima et al. |
| 8,011,905 | B2 | 9/2011 | Artsyukhovich et al. |
| 9,004,886 | B2 | 4/2015 | Beck et al. |
| 9,662,433 | B2 | 5/2017 | Matsuo et al. |
| 10,532,143 | B2 | 1/2020 | Mochizuki |
| 2001/0004444 | A1 | 6/2001 | Haser et al. |
| 2002/0151838 | A1 | 10/2002 | Beck et al. |
| 2003/0040700 | A1 | 2/2003 | Hickle et al. |
| 2003/0071072 | A1 | 4/2003 | Takahashi et al. |
| 2003/0214412 | A1 | 11/2003 | Ho et al. |
| 2005/0025647 | A1 | 2/2005 | Ortega et al. |
| 2007/0217933 | A1 | 9/2007 | Haser et al. |
| 2007/0258838 | A1 | 11/2007 | Drake et al. |
| 2008/0154095 | A1 | 6/2008 | Stubkjaer et al. |
| 2009/0214365 | A1 | 8/2009 | Norman et al. |
| 2009/0312686 | A1* | 12/2009 | Sakamoto ............ A61M 1/3643 604/6.11 |
| 2010/0049134 | A1 | 2/2010 | Schuman, Jr. |
| 2010/0106466 | A1 | 4/2010 | Frohlich et al. |
| 2010/0203179 | A1 | 8/2010 | Kaushik et al. |
| 2011/0033318 | A1 | 2/2011 | Ramirez, Jr. et al. |
| 2011/0130741 | A1 | 6/2011 | Miles et al. |
| 2011/0230814 | A1 | 9/2011 | Kopperschmidt et al. |
| 2012/0082576 | A1 | 4/2012 | Beck et al. |
| 2012/0083737 | A1 | 4/2012 | Beck |
| 2013/0126404 | A1* | 5/2013 | Gronau ................ F04B 49/022 417/63 |
| 2013/0150768 | A1* | 6/2013 | Sakamoto ............ A61M 1/1601 73/40.5 R |
| 2014/0219829 | A1 | 8/2014 | Matsuo et al. |
| 2015/0217040 | A1* | 8/2015 | Matsuo ................ F04B 43/1253 417/477.1 |
| 2015/0238677 | A1 | 8/2015 | Akita et al. |
| 2018/0133384 | A1 | 5/2018 | Tokunaga et al. |

FOREIGN PATENT DOCUMENTS

| | | |
|---|---|---|
| EP | 1947340 A1 | 7/2008 |
| EP | 2749858 A1 | 7/2014 |
| EP | 2752210 A1 | 7/2014 |
| EP | 3069742 A1 | 9/2016 |
| JP | S56-113083 A | 9/1981 |
| JP | S64-022357 A | 2/1989 |
| JP | H03-001290 U1 | 1/1991 |
| JP | H04-015938 U1 | 1/1992 |
| JP | H08-510812 A | 11/1996 |
| JP | 2003-265601 A | 9/2003 |
| JP | 2004-049494 A | 2/2004 |
| JP | 2004-187990 A | 7/2004 |
| JP | 2005-503202 A | 2/2005 |
| JP | 2007-224909 A | 9/2007 |
| JP | 2008-000425 A | 1/2008 |
| JP | 2008-002388 A | 1/2008 |
| JP | 2008-208808 A | 9/2008 |
| JP | 2008-289635 A | 12/2008 |
| JP | 2009-525770 A | 7/2009 |
| JP | 2009285128 A | 12/2009 |
| JP | 2009297193 A | 12/2009 |
| JP | 2010-188170 A | 9/2010 |
| JP | 2010-190062 A | 9/2010 |
| JP | 2010-273693 A | 12/2010 |
| JP | 2011-030880 A | 2/2011 |
| JP | 2012-192099 A | 10/2012 |
| JP | 2012-192100 A | 10/2012 |
| JP | 2015-092977 A | 5/2015 |
| WO | 1994/028309 A1 | 12/1994 |
| WO | 95/10310 A1 | 4/1995 |
| WO | 97/10013 A1 | 3/1997 |
| WO | 2007/072772 A1 | 6/2007 |
| WO | 2007/093064 A1 | 8/2007 |
| WO | 2010/020380 A1 | 2/2010 |
| WO | 2016/020061 A2 | 2/2016 |

OTHER PUBLICATIONS

Potentially related U.S. Appl. No. 15/292,404, filed Oct. 13, 2016, U.S. Pat. No. 10,532,143 issued on Jan. 14, 2020.

Potentially related U.S. Appl. No. 16/811,042, filed Mar. 6, 2020 entitled "Extracorporeal Circulation Apparatus and Method of Discharging Bubbles Therefrom".

* cited by examiner

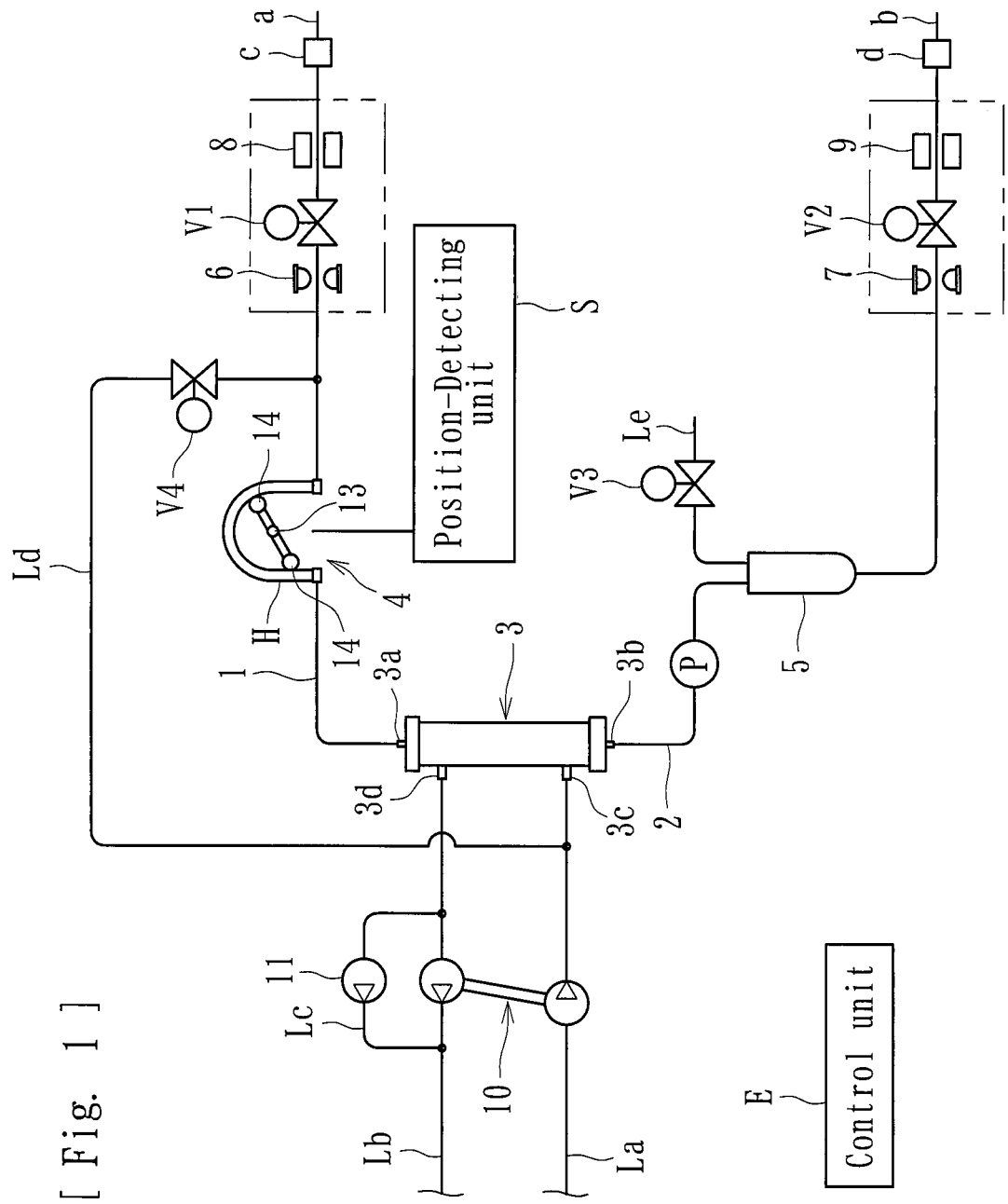
[Fig. 1]

[Fig. 2]
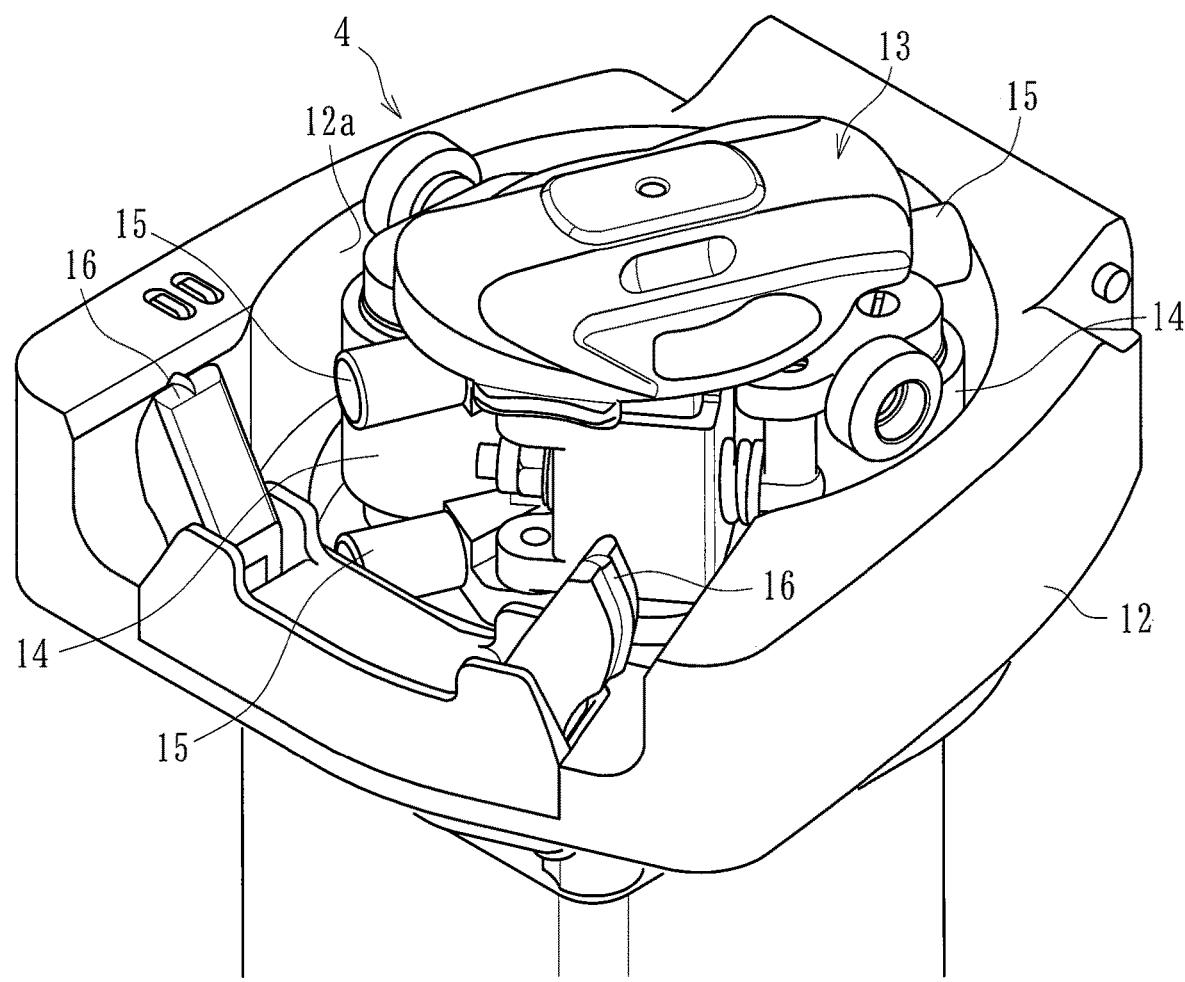

[Fig. 3]
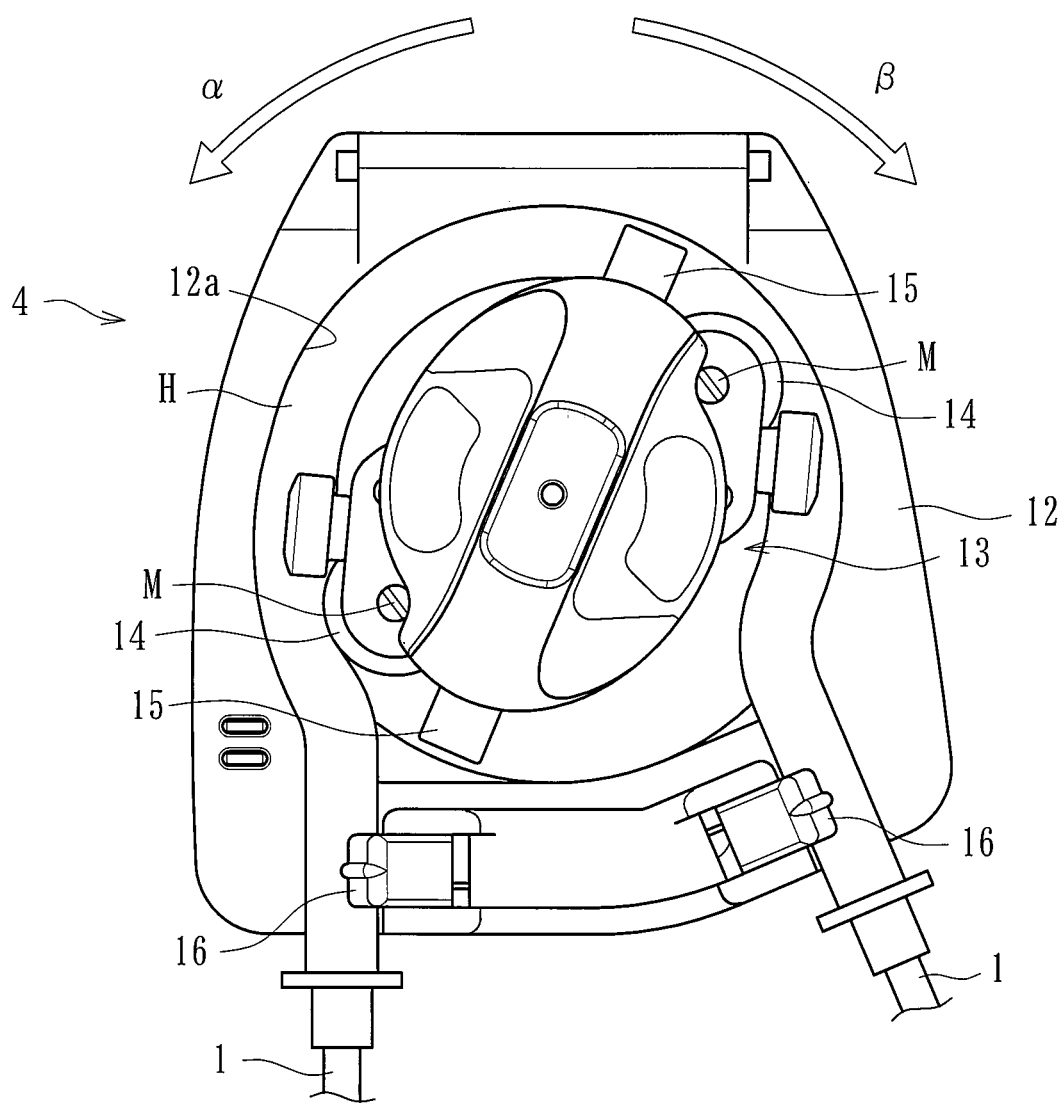

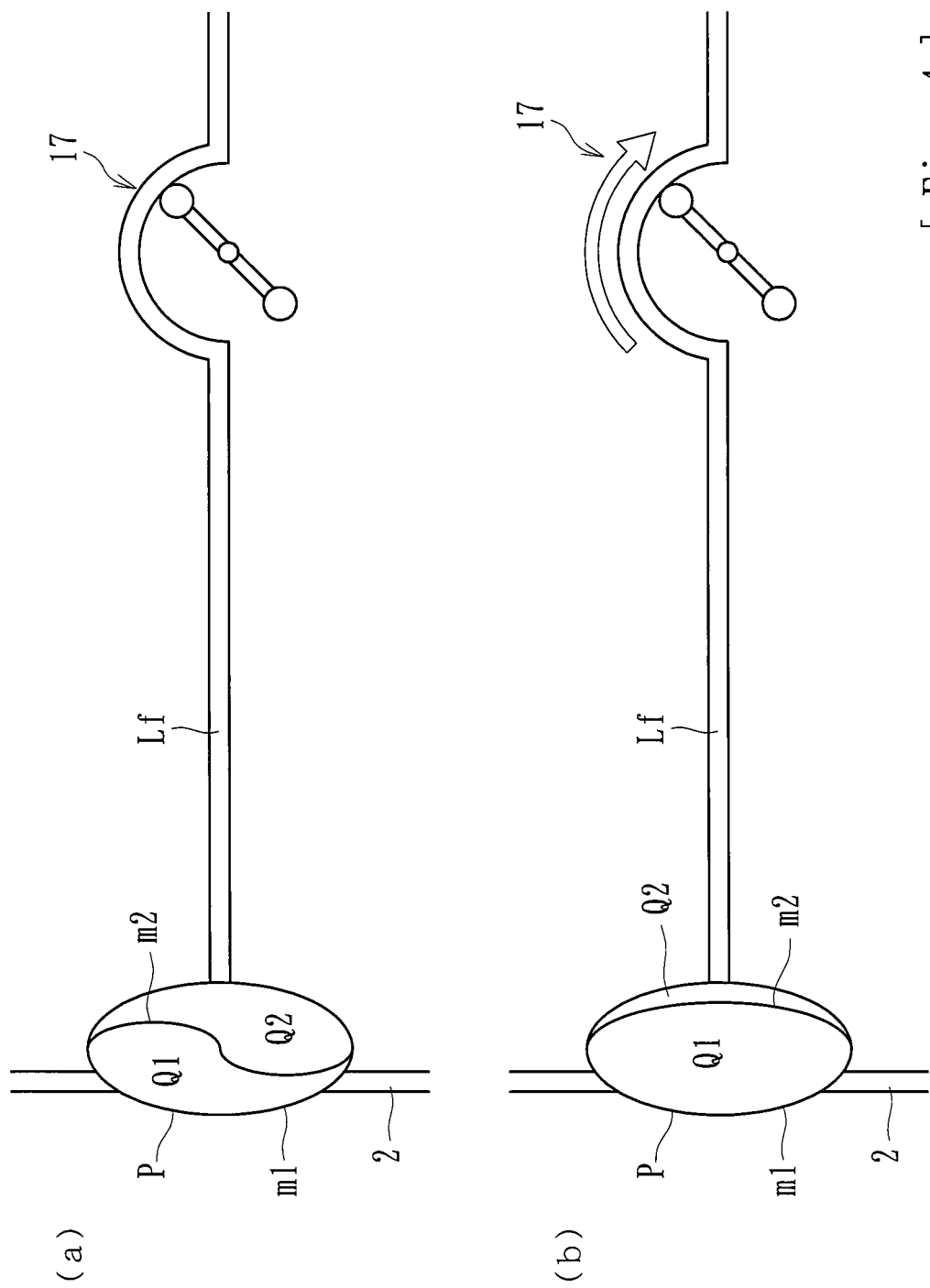
[Fig. 4]

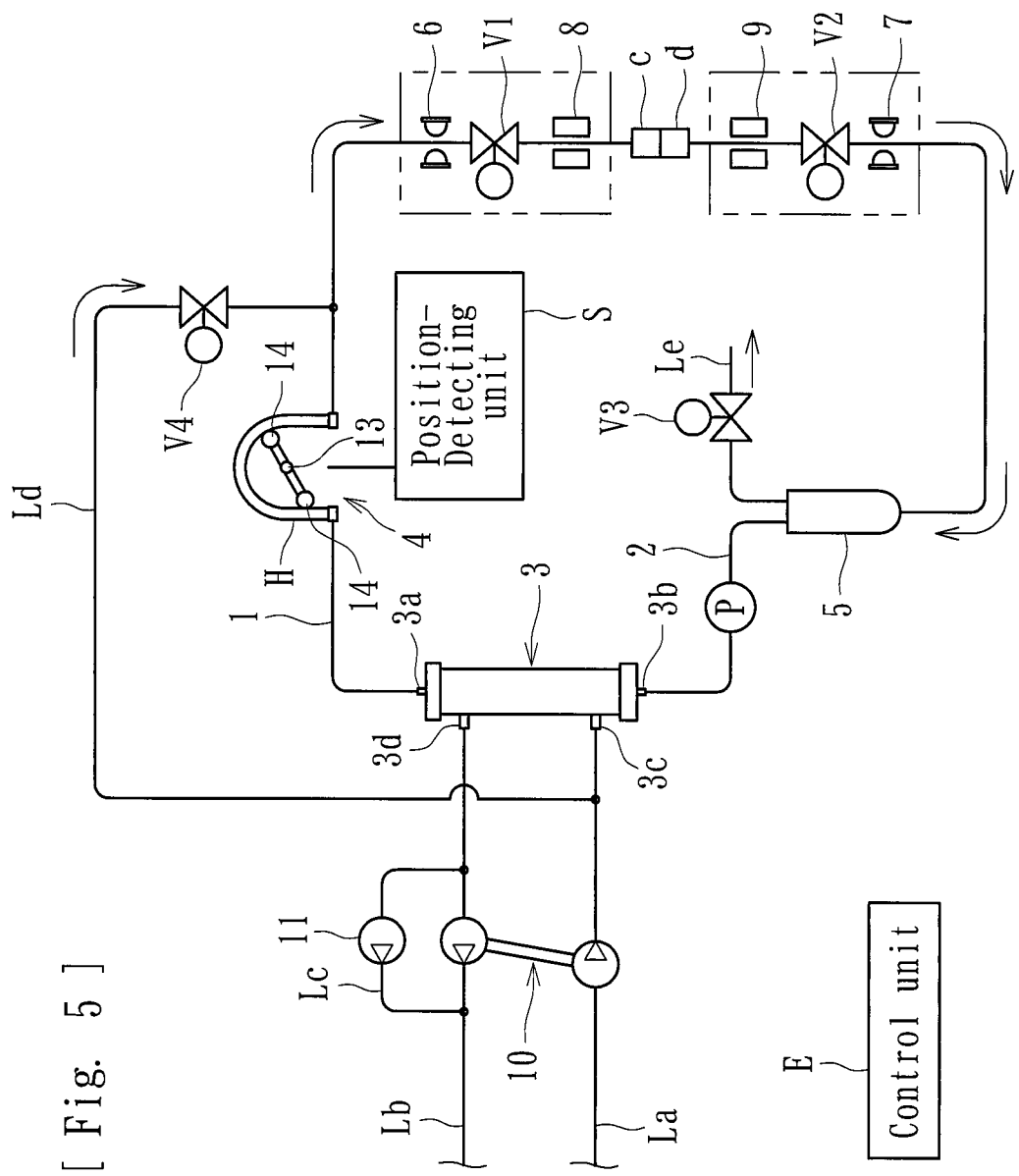
[Fig. 5]

[Fig. 6]
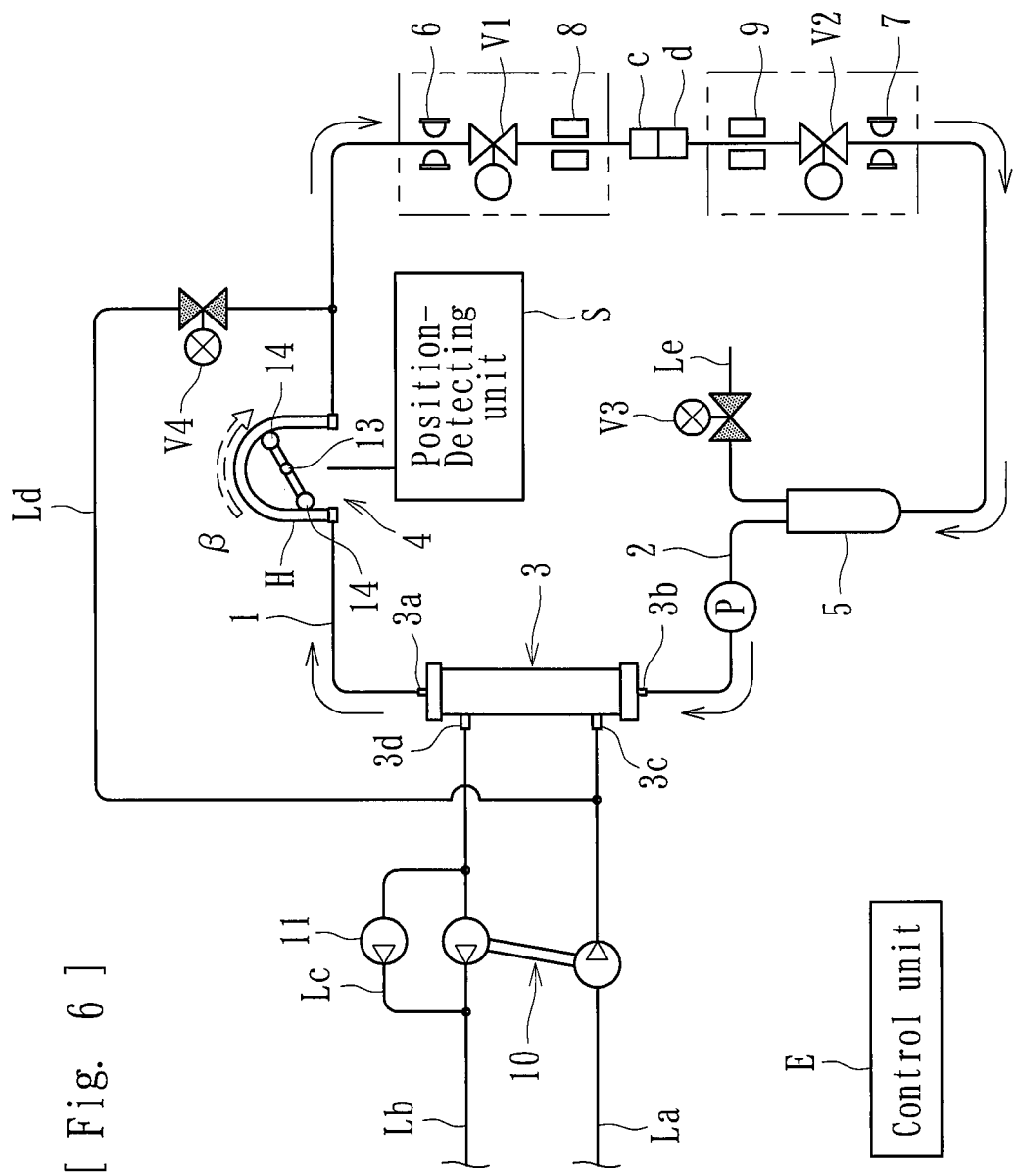

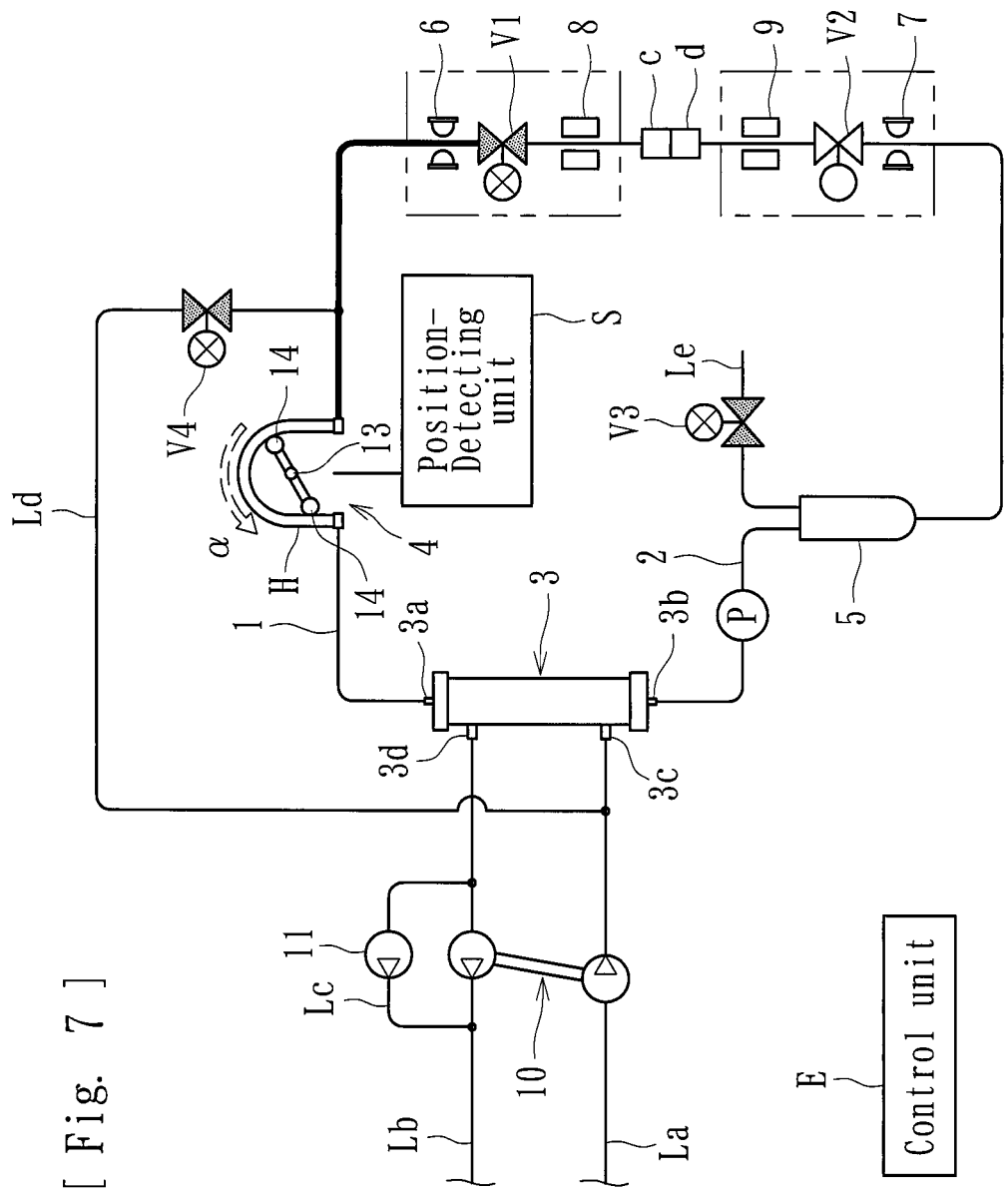
[Fig. 7]

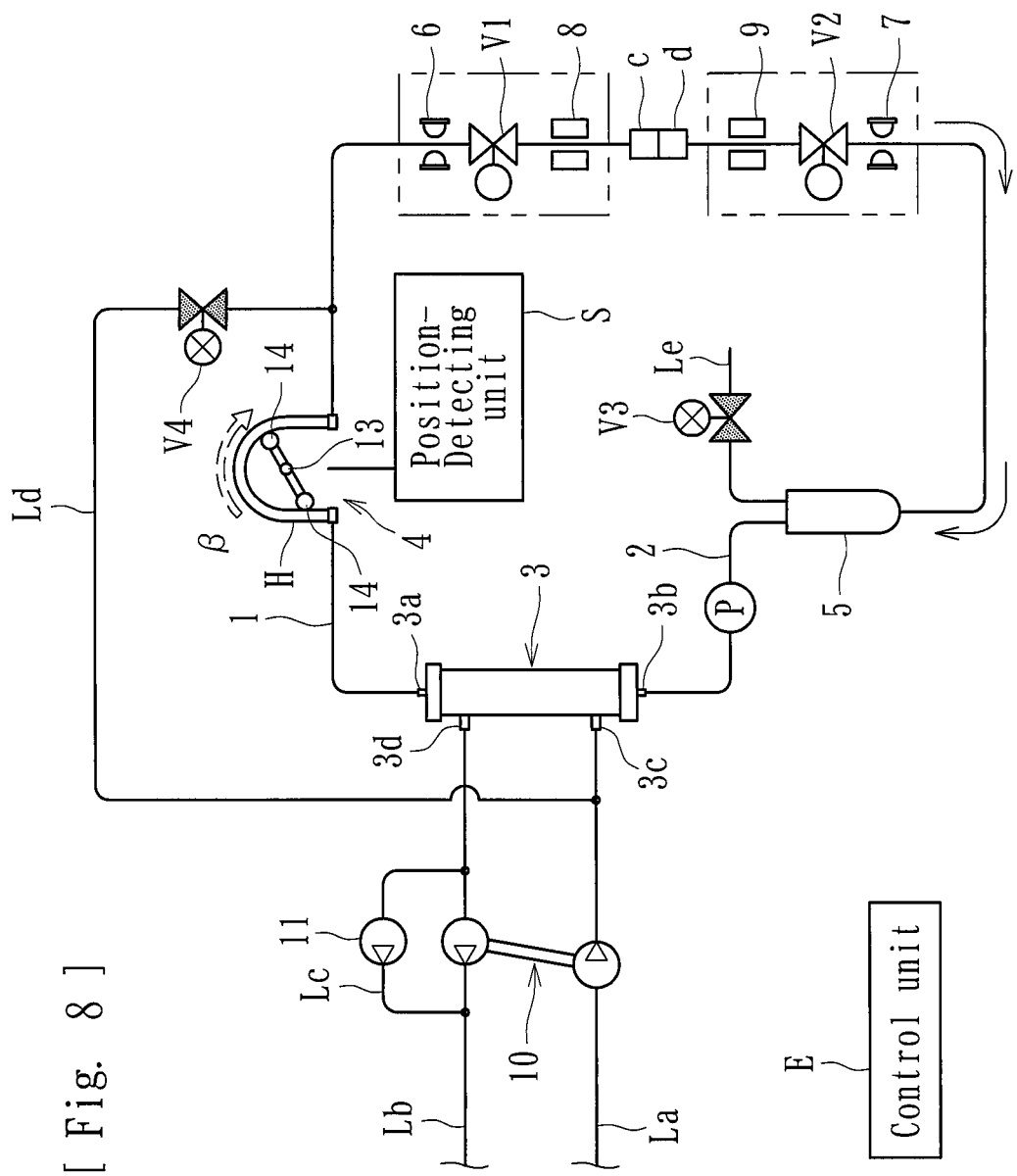

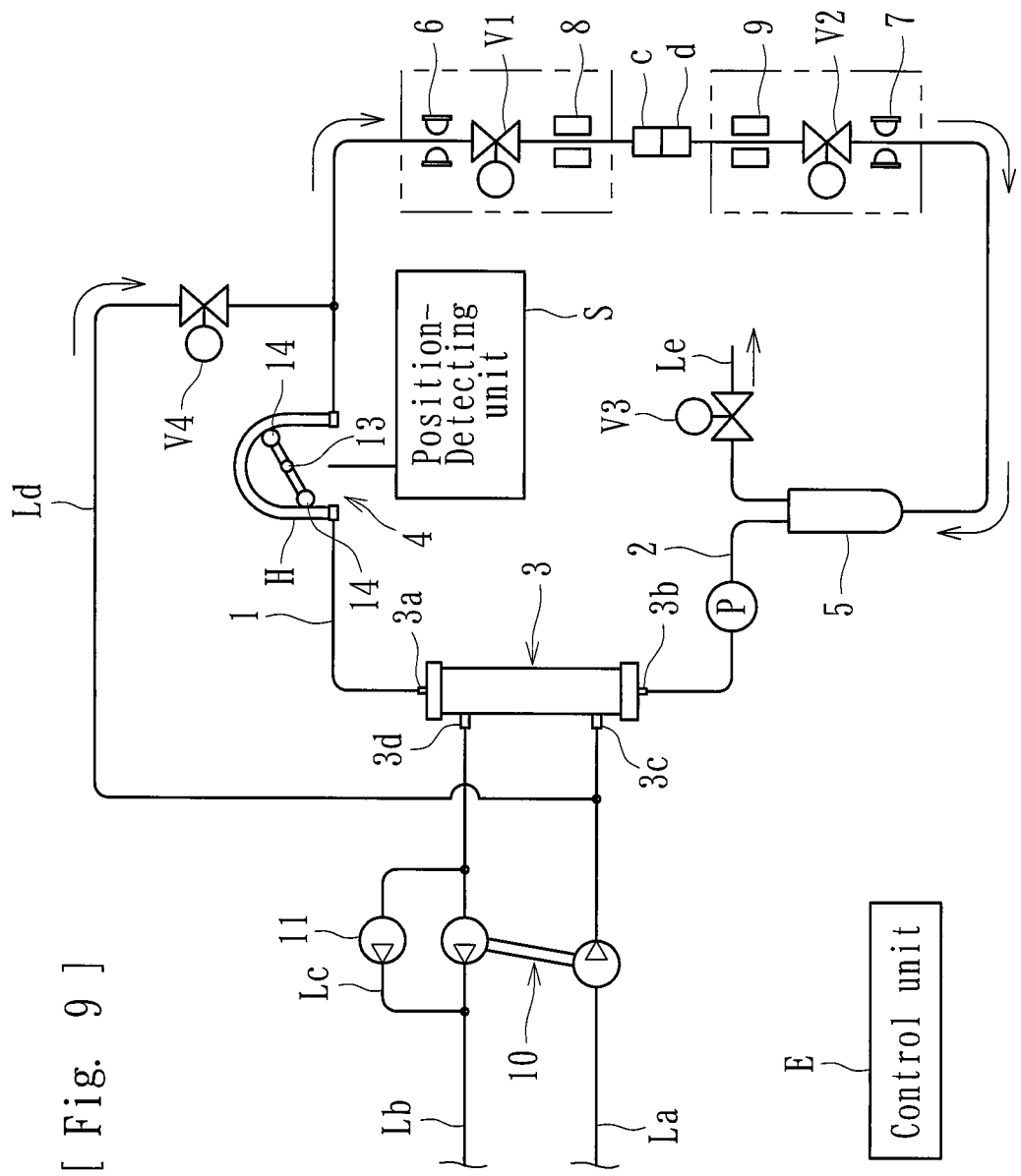
[Fig. 9]

[Fig. 10]
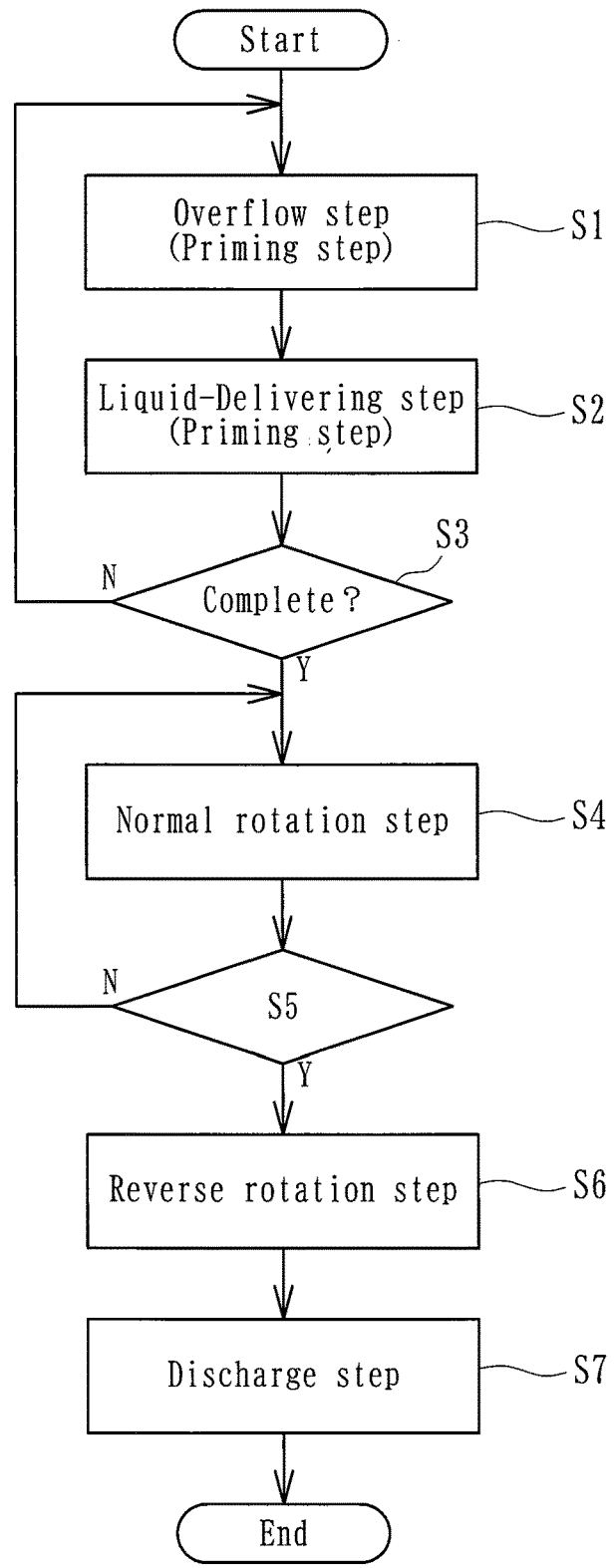
S5: Has roller reached predetermined position?

[Fig. 11]
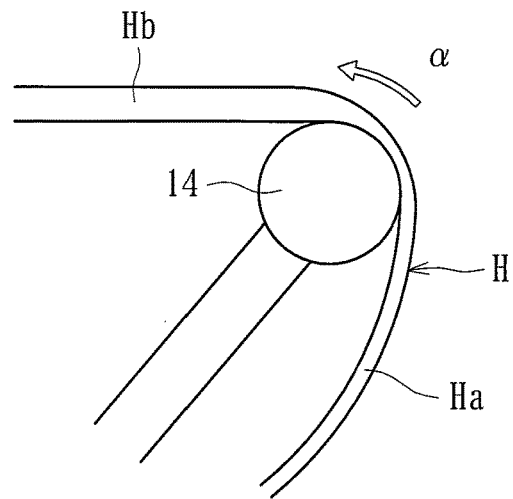
[Fig. 12]
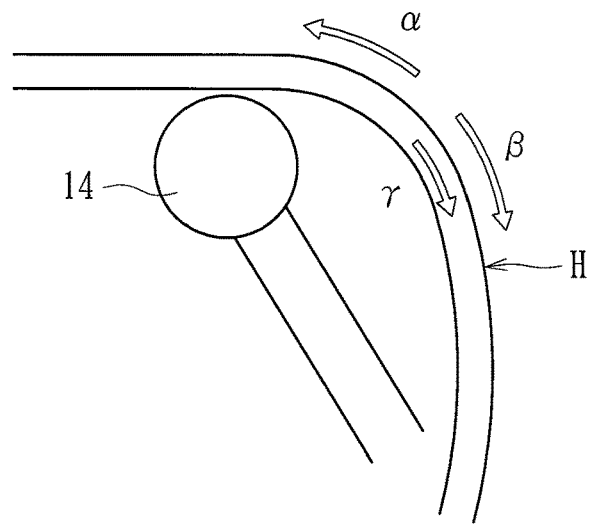
[Fig. 13]
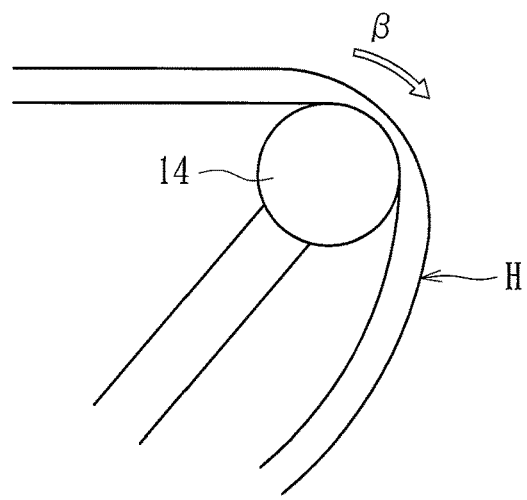

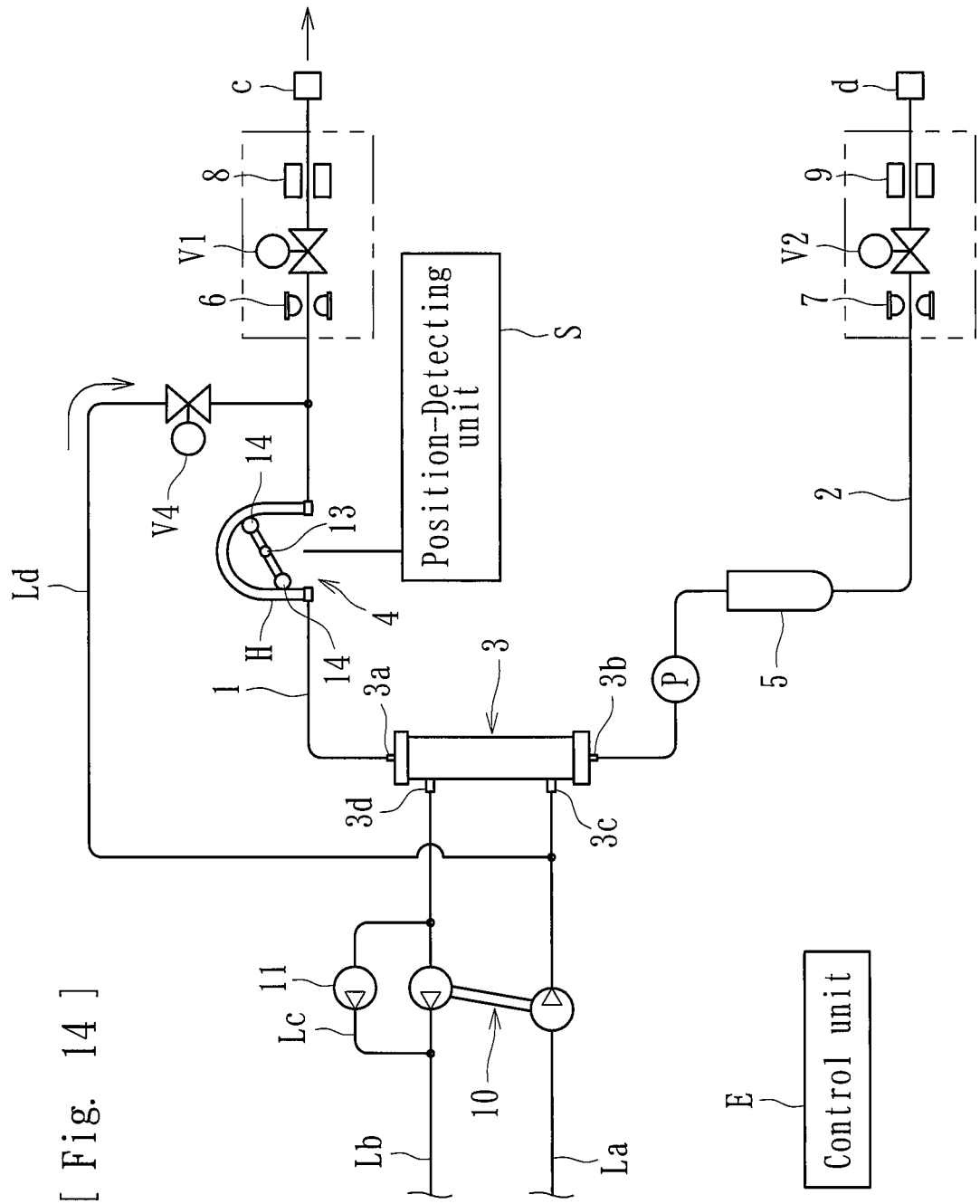
[Fig. 14]

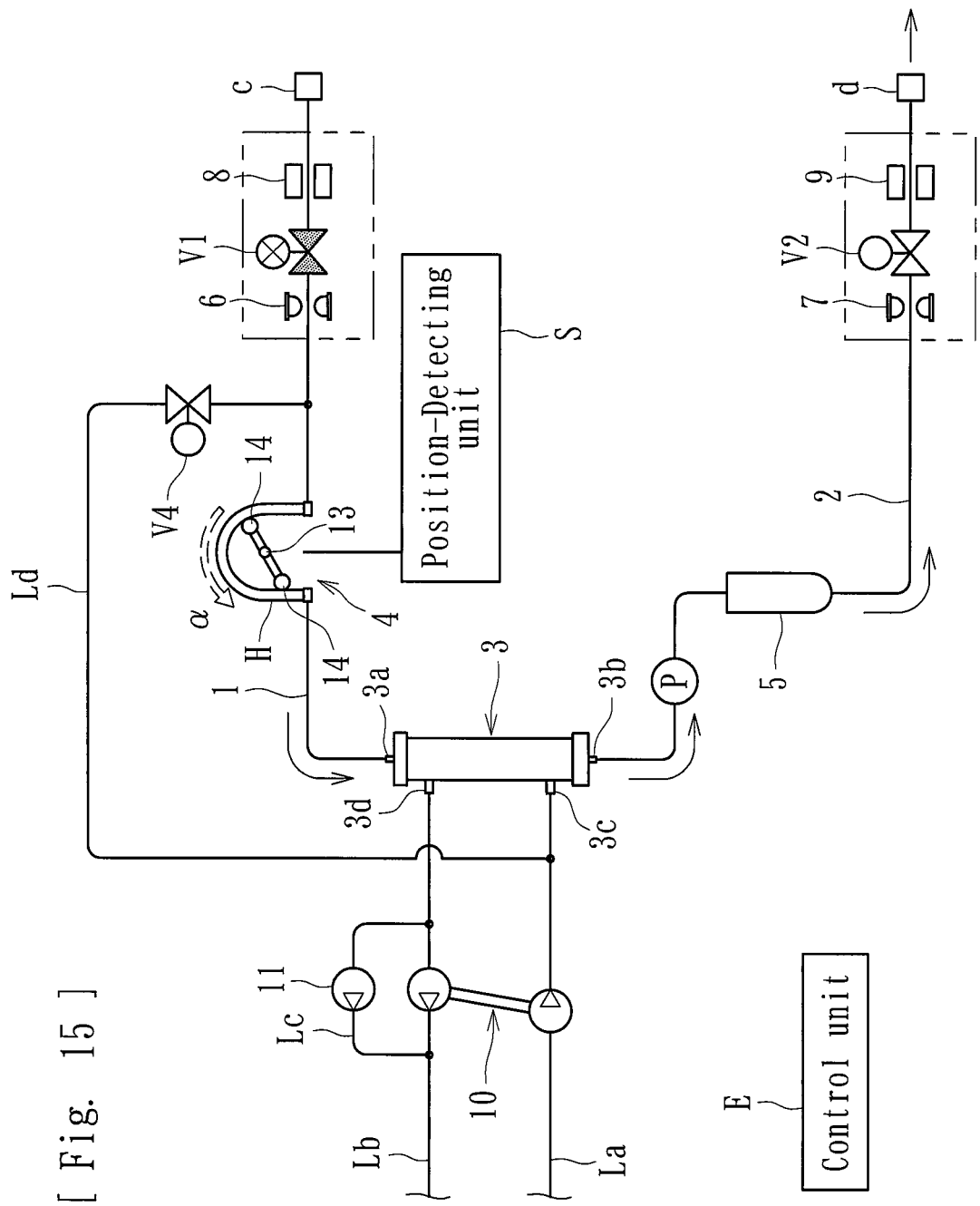
[Fig. 15]

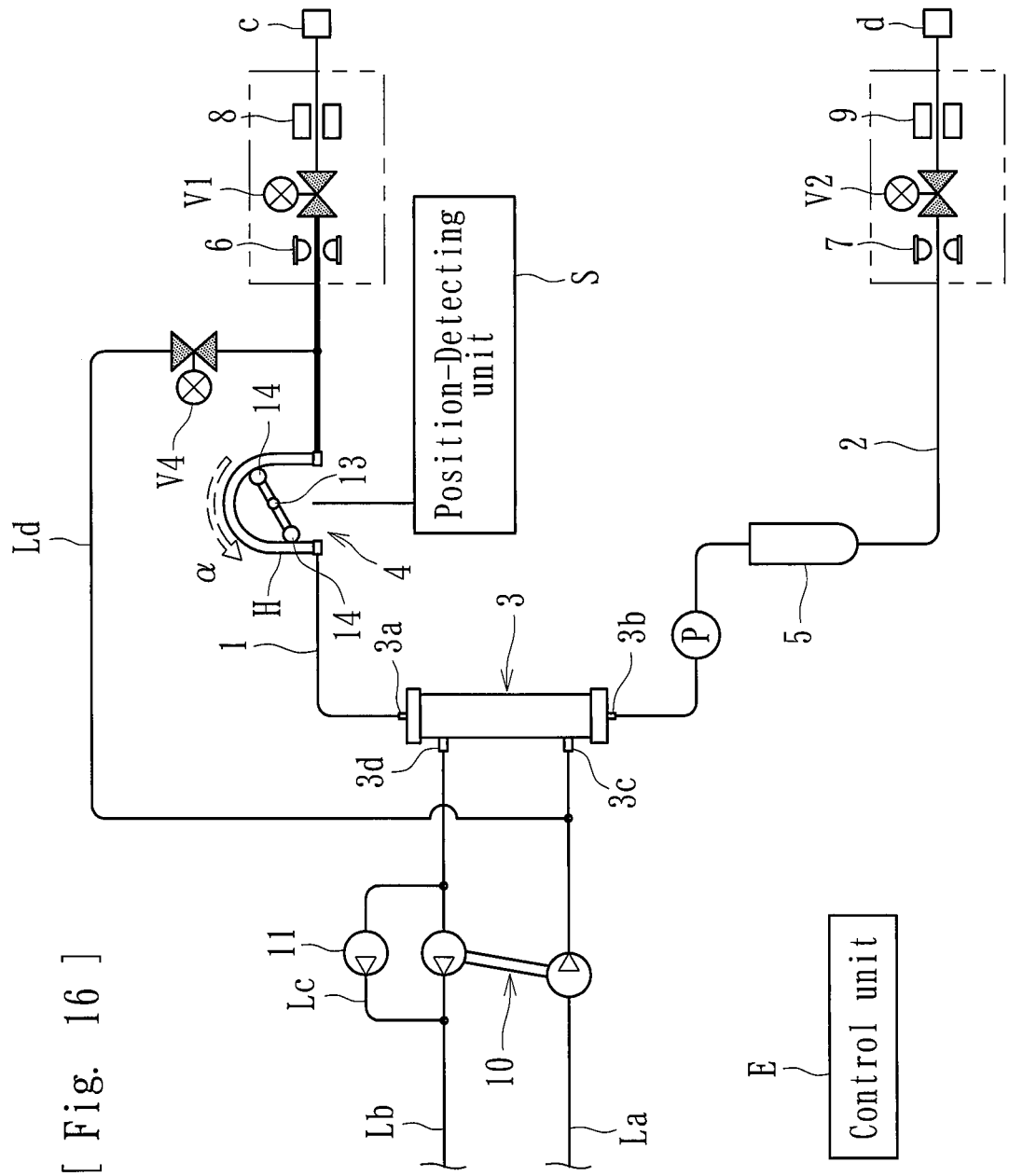
[Fig. 16]

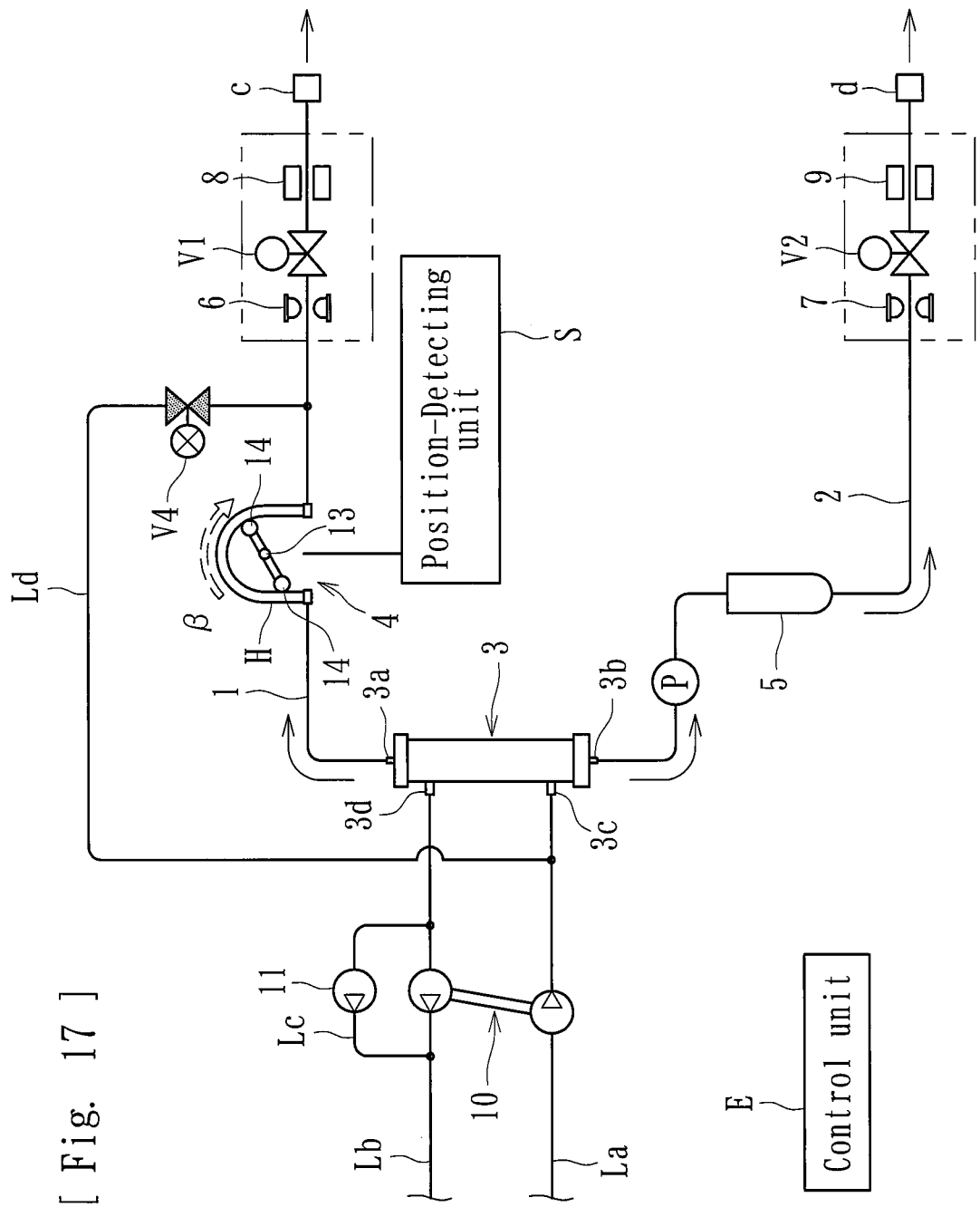
[Fig. 17]

[Fig. 18]
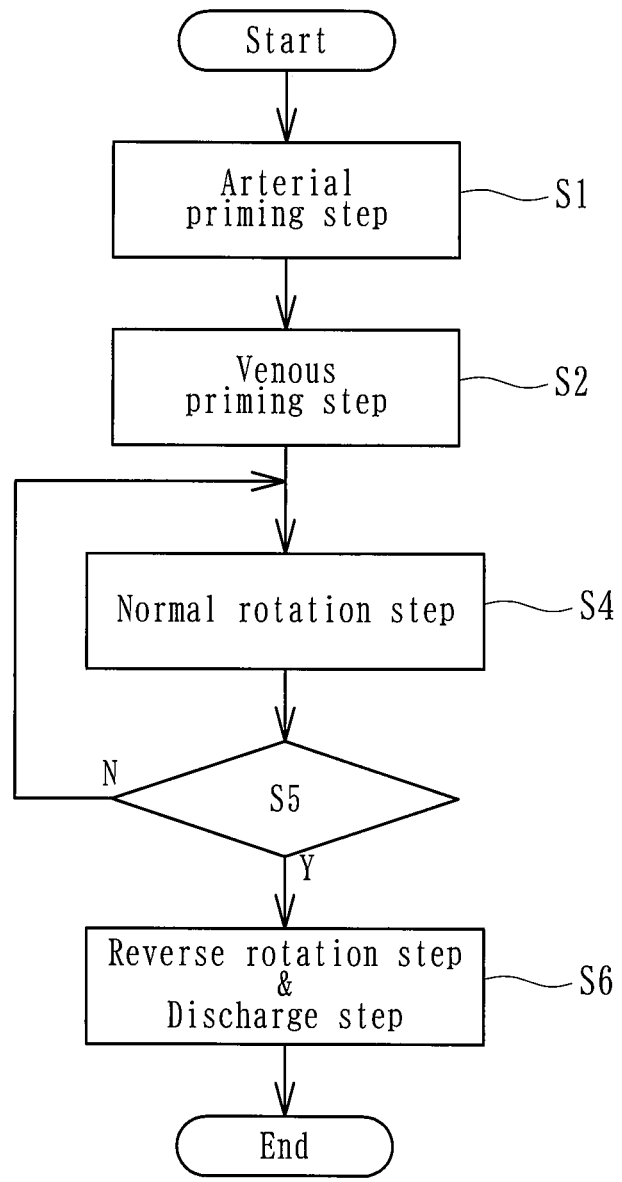
S5: Has roller reached predetermined position?

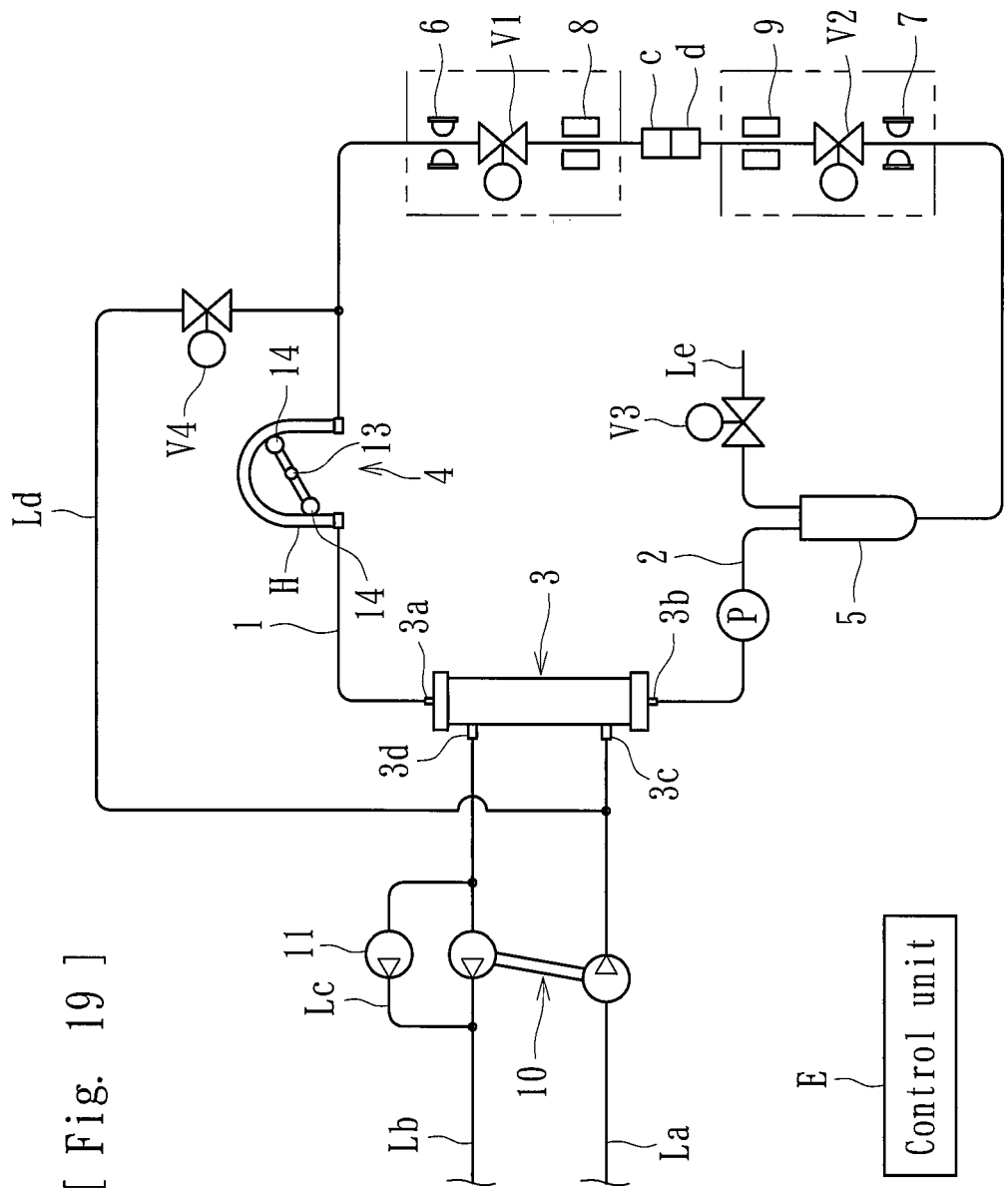

BLOOD PURIFICATION APPARATUS AND METHOD OF DISCHARGING BUBBLES THEREFROM

CROSS-REFERENCE TO RELATED APPLICATION(S)

This application is a continuation of International Application No. PCT/JP2018/033152, filed on Sep. 7, 2018, now published as WO2019/049969 dated Mar. 14, 2019, which claims priority to Japanese Application No. 2017-172562, filed on Sep. 7, 2017, the entire disclosures of which are hereby incorporated by reference.

FIELD

The present invention relates to a blood purification apparatus for purifying a patient's blood while causing the blood to extracorporeally circulate in dialysis treatment or the like performed with a dialyzer, and also relates to a method of discharging bubbles therefrom.

BACKGROUND

In general, dialysis treatment is performed by using a blood circuit for allowing blood collected from a patient to extracorporeally circulate and to be returned into the body. Such a blood circuit basically includes, for example, an arterial blood circuit and a venous blood circuit that are connected to a dialyzer (a blood purification unit) including hollow fiber membranes. The arterial blood circuit and the venous blood circuit are provided at distal ends thereof with an arterial puncture needle and a venous puncture needle, respectively. Extracorporeal circulation of blood in the dialysis treatment is performed with the puncture needles puncturing the patient.

In particular, the arterial blood circuit is provided with a squeezable tube connected thereto and a peristaltic blood pump. The blood pump delivers liquid by squeezing the squeezable tube with a roller. When the blood pump is activated, the patient's blood can be caused to extracorporeally circulate through the blood circuit. Therefore, the blood in extracorporeal circulation undergoes blood purification treatment in the dialyzer.

Furthermore, the arterial blood circuit is provided with a priming-solution supply line for supplying a priming solution to the blood circuit. Before the dialysis treatment, a priming process is performed in which a priming solution is supplied through the priming-solution supply line and is discharged through an overflow line, whereby bubbles in the blood circuit are discharged while flow routes in the blood circuit are filled with the priming solution (see PTL 1, for example).

PTL 1: Japanese Unexamined Patent Application Publication No. 2010-273693, the teachings of which are expressly incorporated by reference herein for all purposes.

SUMMARY

However, in the above known blood purification apparatus, if microbubbles remain in the priming solution particularly in the squeezable tube, a large volume of priming solution may need to be supplied at a high flow rate so as to discharge such microbubbles to the outside of the blood circuit.

Accordingly, the present applicant has found a phenomenon in which when a negative pressure is generated in the squeezable tube by activating the blood pump with a flow route on the suction side being closed, a backflow occurs at the instant that the roller of the blood pump releases the squeezable tube. Such a backflow occurs at a flow rate higher than the flow rate at the activation of the blood pump. In this respect, the present applicant has examined the possibility of smoothly and assuredly discharging residual microbubbles from the squeezable tube with the use of the backflow.

The present invention has been conceived in view of the above circumstances and provides a blood purification apparatus capable of smoothly and assuredly discharging not only microbubbles remaining in a squeezable tube after a priming process but also microbubbles detached from flow routes in a blood circuit and in a blood purification unit with the use of a backflow generated at the instant that a roller of a blood pump releases the squeezable tube, and also provides a method of discharging bubbles therefrom.

According to the teachings herein, there is provided a blood purification apparatus including a blood circuit including an arterial blood circuit and a venous blood circuit and allowing a patient's blood to extracorporeally circulate from a distal end of the arterial blood circuit to a distal end of the venous blood circuit; a blood purification unit connected to a proximal end of the arterial blood circuit and to a proximal end of the venous blood circuit and that purifies the blood flowing through the blood circuit; a squeezable tube connected to the arterial blood circuit; a blood pump formed of a peristaltic pump that delivers liquid by squeezing, with a roller, the squeezable tube while a rotor is driven to rotate, the blood pump delivering the liquid from the distal end of the arterial blood circuit toward the blood purification unit when the rotor is rotated normally such that the roller moves in a lengthwise direction of the squeezable tube, the blood pump delivering the liquid from the blood purification unit toward the distal end of the arterial blood circuit when the rotor is rotated reversely such that the roller moves in the lengthwise direction of the squeezable tube; a discharge unit through which a priming solution supplied into the blood circuit is discharged to an outside; a closing unit that generates a negative pressure in the squeezable tube at the normal rotation of the rotor of the blood pump by closing a region of the blood pump that is filled with the priming solution; and a control unit that controls the blood pump and the closing unit. The control unit executes a priming step in which the priming solution supplied into the blood circuit is discharged through the discharge unit while a flow route in the blood circuit is filled with the priming solution; a normal rotation step in which, after the priming step, the region filled with the priming solution is closed by the closing unit, and the rotor of the blood pump is rotated normally until the roller of the blood pump releases the squeezable tube to generate a backflow; a reverse rotation step in which, after the backflow is generated in the normal rotation step at the release of the squeezable tube by the roller of the blood pump, bubbles are moved by reversely rotating the rotor while disabling the closing by the closing unit; and a discharge step in which the bubbles moved in the reverse rotation step are discharged through the discharge unit.

According to the teachings herein, the blood purification apparatus taught herein further includes a detecting unit that detects a position where the roller of the blood pump releases the squeezable tube.

According to the teachings herein, in the blood purification apparatus taught herein, the detecting unit is formed of a position-detecting unit that detects a position of the roller.

According to the teachings herein, in the blood purification taught herein, the detecting unit is formed of a pressure-detecting unit that detects a pressure in the blood circuit, the pressure changing with the normal rotation of the roller.

According to the teachings herein, in the blood purification apparatus taught herein, the venous blood circuit is provided with an air-trap chamber connected thereto. Furthermore, the discharge unit is formed of an overflow line extending from a top of the air-trap chamber.

According to the teachings herein, in the blood purification apparatus taught herein, the discharge unit is formed of the distal end of the arterial blood circuit or the distal end of the venous blood circuit.

According to the teachings herein, there is provided a method of discharging bubbles from a blood purification apparatus. The apparatus includes a blood circuit including an arterial blood circuit and a venous blood circuit and allowing a patient's blood to extracorporeally circulate from a distal end of the arterial blood circuit to a distal end of the venous blood circuit; a blood purification unit connected to a proximal end of the arterial blood circuit and to a proximal end of the venous blood circuit and that purifies the blood flowing through the blood circuit; a squeezable tube connected to the arterial blood circuit; a blood pump formed of a peristaltic pump that delivers liquid by squeezing, with a roller, the squeezable tube while a rotor is driven to rotate, the blood pump delivering the liquid from the distal end of the arterial blood circuit toward the blood purification unit when the rotor is rotated normally such that the roller moves in a lengthwise direction of the squeezable tube, the blood pump delivering the liquid from the blood purification unit toward the distal end of the arterial blood circuit when the rotor is rotated reversely such that the roller moves in the lengthwise direction of the squeezable tube; a discharge unit through which a priming solution supplied into the blood circuit is discharged to an outside; and a closing unit that generates a negative pressure in the squeezable tube at the normal rotation of the rotor of the blood pump by closing a region of the blood pump that is filled with the priming solution. The method includes a priming step in which the priming solution supplied into the blood circuit is discharged through the discharge unit while a flow route in the blood circuit is filled with the priming solution; a normal rotation step in which, after the priming step, the region filled with the priming solution is closed by the closing unit, and the rotor of the blood pump is rotated normally until the roller of the blood pump releases the squeezable tube to generate a backflow; a reverse rotation step in which, after the backflow is generated in the normal rotation step at the release of the squeezable tube by the roller of the blood pump, bubbles are moved by reversely rotating the rotor while disabling the closing by the closing unit; and a discharge step in which the bubbles moved in the reverse rotation step are discharged through the discharge unit.

According to the teachings herein, in the method of discharging bubbles from the blood purification apparatus taught herein, the blood purification apparatus further includes a detecting unit that detects a position where the roller of the blood pump releases the squeezable tube.

According to the teachings herein, in the method of discharging bubbles from the blood purification apparatus taught herein, the detecting unit is formed of a position-detecting unit that detects a position of the roller.

According to the teachings herein, in the method of discharging bubbles from the blood purification apparatus taught herein, the detecting unit is formed of a pressure-detecting unit that detects a pressure in the blood circuit, the pressure changing with the normal rotation of the roller.

According to the teachings herein, in the method of discharging bubbles from the blood purification apparatus taught herein, the venous blood circuit is provided with an air-trap chamber connected thereto. Furthermore, the discharge unit is formed of an overflow line extending from a top of the air-trap chamber.

According to the teachings herein, in the method of discharging bubbles from the blood purification apparatus taught herein, the discharge unit is formed of the distal end of the arterial blood circuit or the distal end of the venous blood circuit.

According to the teachings herein, after the priming step, the normal rotation step is executed in which the region filled with the priming solution is closed by the closing unit and the rotor of the blood pump is rotated normally until the roller of the blood pump releases the squeezable tube to generate a backflow. Therefore, with the use of the backflow generated at the instant that the roller of the blood pump has released the squeezable tube, not only microbubbles remaining in the squeezable tube after the priming step but also microbubbles detached from the flow routes in the blood circuit and in the blood purification unit can be discharged smoothly and assuredly.

According to the teachings herein, the blood purification apparatus includes the detecting unit that detects the position where the roller of the blood pump releases the squeezable tube. Therefore, immediately after the backflow is generated, the normal rotation step can be ended for the subsequent reverse rotation step. Hence, bubbles moved along with the backflow are prevented from moving backward and can be discharged through the discharge unit.

According to the teachings herein, the detecting unit is formed of the position detecting unit that detects the position of the roller. Therefore, the position where the roller of the blood pump releases the squeezable tube to generate a backflow can be precisely detected by the position-detecting unit.

According to the teachings herein, the detecting unit is formed of the pressure-detecting unit that detects the pressure in the blood circuit, the pressure changing with the normal rotation of the roller. Therefore, the position where the roller of the blood pump releases the squeezable tube to generate a backflow can be detected with the use of the pressure-detecting unit, which is necessary for blood purification treatment.

According to the teachings herein, the venous blood circuit is provided with the air-trap chamber. Furthermore, the discharge unit is formed of the overflow line extending from the top of the air-trap chamber connected thereto. Therefore, when the priming step is executed with the distal end of the arterial blood circuit and the distal end of the venous blood circuit being connected to each other, not only microbubbles remaining in the squeezable tube but also microbubbles detached from the flow routes in the blood circuit and in the blood purification unit can be discharged in a good manner through the overflow line.

According to the teachings herein, the discharge unit is formed of the distal end of the arterial blood circuit or the distal end of the venous blood circuit. Therefore, when the priming step is executed without connecting the distal end of the arterial blood circuit and the distal end of the venous blood circuit to each other, not only microbubbles remaining in the squeezable tube but also microbubbles detached from the flow routes in the blood circuit and in the blood purification unit can be discharged in a good manner from the distal end of the arterial blood circuit or the distal end of the venous blood circuit.

BRIEF DESCRIPTION OF THE DRAWINGS

FIG. 1 is a schematic diagram of a dialysis apparatus (a blood purification apparatus) according to a first embodiment of the present invention.

FIG. 2 is a perspective view of a blood pump applied to the dialysis apparatus.

FIG. 3 is a plan view of the blood pump with a squeezable tube attached thereto.

FIG. 4 includes schematic diagrams of a venous-pressure-measuring unit applied to the dialysis apparatus.

FIG. 5 is a schematic diagram of the dialysis apparatus executing a priming step (an overflow step).

FIG. 6 is a schematic diagram of the dialysis apparatus executing the priming step (a liquid-delivering step).

FIG. 7 is a schematic diagram of the dialysis apparatus executing a normal rotation step.

FIG. 8 is a schematic diagram of the dialysis apparatus executing a reverse rotation step.

FIG. 9 is a schematic diagram of the dialysis apparatus executing a discharge step.

FIG. 10 is a flow chart illustrating a control process executed by a control unit of the dialysis apparatus.

FIG. 11 is a schematic diagram illustrating a state where a roller of the blood pump is squeezing a squeezable tube in the normal rotation step executed in the dialysis apparatus.

FIG. 12 is a schematic diagram illustrating a state where the roller of the blood pump has just released the squeezable tube in the normal rotation step executed in the dialysis apparatus.

FIG. 13 is a schematic diagram illustrating a state where the roller of the blood pump is squeezing the squeezable tube in the reverse rotation step executed in the dialysis apparatus.

FIG. 14 is a schematic diagram of a dialysis apparatus (a blood purification apparatus) according to a second embodiment of the present invention that is executing a priming step (an arterial priming step).

FIG. 15 is a schematic diagram of the dialysis apparatus executing the priming step (a venous priming step).

FIG. 16 is a schematic diagram of the dialysis apparatus executing a normal rotation step.

FIG. 17 is a schematic diagram of the dialysis apparatus executing a reverse rotation step and a discharge step.

FIG. 18 is a flow chart illustrating a control process executed by a control unit of the dialysis apparatus.

FIG. 19 is a schematic diagram of a dialysis apparatus according to another embodiment of the present invention.

DETAILED DESCRIPTION

Embodiments of the present invention will now be described specifically with reference to the drawings.

A blood purification apparatus according to a first embodiment is a dialysis apparatus intended for dialysis treatment and basically includes, as illustrated in FIG. 1, a blood circuit formed of an arterial blood circuit 1 and a venous blood circuit 2, a dialyzer 3 (a blood purification unit) connected to a proximal end of the arterial blood circuit 1 and to a proximal end of the venous blood circuit 2 and that purifies blood flowing through the blood circuit, an air-trap chamber 5 connected to the venous blood circuit 2, a priming-solution supply line Ld connected to the arterial blood circuit 1 and through which a priming solution is supplied into the blood circuit, an overflow line Le (a discharge unit) through which the priming solution supplied into the blood circuit through the priming-solution supply line Ld is discharged to the outside, a closing unit (in the present embodiment, an electromagnetic valve V1) that closes a region filled with the priming solution in the blood circuit and thus generates a negative pressure in a squeezable tube H when a rotor 13 of a blood pump 4 is rotated normally, and a control unit E that controls the blood pump 4 and the closing unit (the electromagnetic valve V1).

The arterial blood circuit 1 is provided with an arterial puncture needle (a) connected to a distal end thereof through a connector (c), and with the blood pump 4, which is of a peristaltic type, at a halfway position thereof. The venous blood circuit 2 is provided with a venous puncture needle (b) connected to a distal end thereof through a connector (d), and with an air-trap chamber 5 at a halfway position thereof. Furthermore, the arterial blood circuit 1 and the venous blood circuit 2 are provided in respective distal portions thereof (near the respective connectors c and d) with respective electromagnetic valves V1 and V2, which close or open respective flow routes.

When the blood pump 4 is activated with the arterial puncture needle a and the venous puncture needle b being stuck in the patient, the patient's blood flows through the arterial blood circuit 1 and reaches the dialyzer 3, where the blood is purified. Then, the blood flows through the venous blood circuit 2 while undergoing bubble removal in the air-trap chamber 5 and returns into the patient's body. That is, blood purification treatment is performed by purifying the patient's blood with the dialyzer 3 while causing the blood to extracorporeally circulate through the blood circuit from the distal end of the arterial blood circuit 1 to the distal end of the venous blood circuit 2. In this specification, the side of the puncture needle for blood removal (blood collection) is referred to as the "arterial" side, and the side of the puncture needle for blood return is referred to as the "venous" side. The "arterial" side and the "venous" side are not defined in accordance with which of the artery and the vein is to be the object of puncture.

The arterial blood circuit 1 is provided at a halfway position thereof (between the connection to the priming-solution supply line Ld and the dialyzer 3) with a squeezable tube H, which is attachable to the blood pump 4 (specifically, to a fitting recess 12a provided in a stator 12 of the blood pump 4, which will be described in detail below with reference to FIGS. 2 and 3). The squeezable tube H is to be squeezed in the lengthwise direction while being compressed in the radial direction by rollers 14 (a squeezing unit) of the blood pump 4 (the peristaltic pump), whereby liquid in the squeezable tube H is caused to flow in the direction of rotation of a rotor 13. The squeezable tube H is a flexible tube that is softer and has a greater diameter than other flexible tubes forming the arterial blood circuit 1.

As illustrated in FIGS. 2 and 3, the blood pump 4 according to the present embodiment basically includes the stator 12, the rotor 13 that rotates on the inner side of the stator 12, the rollers 14 provided on the rotor 13, a pair of upper and lower guide pins 15, and holding portions 16 that hold and secure the squeezable tube H. In the drawings, a cover provided over the stator 12 of the blood pump 4 is not illustrated.

The stator 12 has the fitting recess 12a, into which the squeezable tube H is to be fitted. As illustrated in FIGS. 2 and 3, the squeezable tube H is fitted along the inner peripheral wall of the fitting recess 12a. The rotor 13, which is rotatably driven by a motor, is provided substantially in the center of the fitting recess 12a. The pair of (two) rollers 14 and the guide pins 15 are provided on a side face (a surface facing the inner peripheral wall of the fitting recess 12a) of the rotor 13.

The rollers 14 are rotatable on respective rotating shafts M (see FIG. 3) provided on the outer peripheral edge of the rotor 13. The rollers 14 compress the squeezable tube H, fitted in the fitting recess 12a, in the radial direction and squeeze the squeezable tube H in the lengthwise direction (the direction of blood flow) with the rotation of the rotor 13, whereby the blood is caused to flow through the arterial blood circuit 1. Specifically, when the rotor 13 is rotated with the squeezable tube H fitted in the fitting recess 12a, the squeezable tube H is compressed between each of the rollers 14 and the inner peripheral wall of the fitting recess 12a. With the rotation of the rotor 13, the squeezable tube H can be squeezed in the direction of rotation of the rotor 13 (in the lengthwise direction of the squeezable tube H). With such a squeezing motion, the blood in the arterial blood circuit 1 is delivered in the direction of rotation of the rotor 13. Thus, the blood can be caused to extracorporeally circulate through the arterial blood circuit 1.

In the blood pump 4 according to the present embodiment, when the rotor 13 is rotated normally and causes the rollers 14 to rotate in the same direction (a direction indicated by reference character α in FIG. 3) in such a manner as to move in the lengthwise direction of the squeezable tube H, the liquid can be delivered from the distal end of the arterial blood circuit 1 toward the dialyzer 3 (the blood purification unit). When the rotor 13 is rotated reversely and causes the rollers 14 to rotate in the same direction (a direction indicated by reference character β in FIG. 3) in such a manner as to move in the lengthwise direction of the squeezable tube H, the liquid can be delivered from the dialyzer 3 (the blood purification unit) toward the distal end of the arterial blood circuit 1.

As illustrated in FIG. 2, the guide pins 15 are a pair of upper and lower pin-like members projecting from the upper end and the lower end, respectively, of the rotor 13 toward the inner peripheral wall of the fitting recess 12a. The squeezable tube H is to be held between the pair of upper and lower guide pins 15. Specifically, while the rotor 13 is rotated, the pair of upper and lower guide pins 15 retain the squeezable tube H at a proper position and prevent the squeezable tube H from being displaced upward or downward from the fitting recess 12a.

The blood pump 4 according to the present embodiment is provided with a position-detecting unit S that detects the positions of the rollers 14. The position-detecting unit S is capable of detecting the position of each roller 14 by detecting, for example, the angle of rotation of the rotor 13. Thus, the position-detecting unit S detects the position where the roller 14 of the blood pump 4 has released the squeezable tube H (see FIG. 12).

The air-trap chamber 5 is provided with the overflow line Le (the discharge unit). The overflow line Le extends from the top of the air-trap chamber 5 with the distal end thereof being open to the atmosphere. The overflow line Le allows the liquid (the priming solution) overflowing from the air-trap chamber 5 to be discharged to the outside. The overflow line Le is provided with an electromagnetic valve V3, which is capable of closing or opening the flow route in the overflow line Le at an arbitrary timing.

The dialyzer 3 has, in a housing thereof, a blood inlet 3a (a blood introduction port), a blood outlet 3b (a blood delivery port), a dialysate inlet 3c (an inlet of a dialysate flow route, or a dialysate introduction port), and a dialysate outlet 3d (an outlet of the dialysate flow route, or a dialysate delivery port). The blood inlet 3a is connected to the proximal end of the arterial blood circuit 1. The blood outlet 3b is connected to the proximal end of the venous blood circuit 2. The dialysate inlet 3c and the dialysate outlet 3d are connected to a dialysate introduction line La and a dialysate drain line Lb, respectively, extending from a dialysis-apparatus body.

The dialyzer 3 houses a plurality of hollow fibers (not illustrated). The hollow fibers form blood purification membranes for purifying the blood. The blood purification membranes in the dialyzer 3 define blood flow routes (each extending between the blood inlet 3a and the blood outlet 3b) through which the patient's blood flows and dialysate flow routes (each extending between the dialysate inlet 3c and the dialysate outlet 3d) through which dialysate flows. The hollow fibers forming the blood purification membranes each have a number of very small holes (pores) extending therethrough from the outer peripheral surface to the inner peripheral surface, thereby forming a hollow fiber membrane. Impurities and the like contained in the blood permeate through the follow fiber membranes into the dialysate.

A duplex pump 10 is provided over the dialysate introduction line La and the dialysate drain line Lb in the dialysis-apparatus body. The dialysate drain line Lb is provided with a bypass line Lc that bypasses the duplex pump 10. The bypass line Lc is provided with an ultrafiltration pump 11 for removing water from the patient's blood flowing through the dialyzer 3. One end of the dialysate introduction line La is connected to the dialyzer 3 (the dialysate inlet 3c), and the other end is connected to a dialysate supply device (not illustrated) that prepares a dialysate at a predetermined concentration. One end of the dialysate drain line Lb is connected to the dialyzer 3 (the dialysate outlet 3d), and the other end is connected to a drainage unit, not illustrated. The dialysate supplied from the dialysate supply device flows through the dialysate introduction line La into the dialyzer 3, and further flows through the dialysate drain line Lb into the drainage unit.

One end of the priming-solution supply line Ld is connected to a predetermined position of the dialysate introduction line La between the duplex pump 10 and the dialyzer 3, and the other end is connected to a predetermined position of the arterial blood circuit 1 between the blood pump 4 and an arterial bubble-detecting unit 6. The priming-solution supply line Ld is provided with an electromagnetic valve V4 that closes or opens a corresponding flow route at an arbitrary timing. When the electromagnetic valve V4 is opened, the dialysate (the priming solution) in the dialysate introduction line La is supplied to the arterial blood circuit 1.

The arterial blood circuit 1 is provided on the distal portion thereof with the arterial bubble-detecting unit 6, which detects bubbles in the liquid flowing through a corresponding position. The venous blood circuit 2 is provided on the distal portion thereof with a venous bubble-detecting unit 7, which detects bubbles in the liquid flowing through a corresponding position. Reference numerals 8 and 9 in the drawing denote blood identifiers provided on the respective distal portions of the arterial blood circuit 1 and the venous blood circuit 2.

Furthermore, the venous blood circuit 2 according to the present embodiment is provided with a venous-pressure-measuring unit P that measures venous pressure. The venous-pressure-measuring unit P is provided at a position of the venous blood circuit 2 between the dialyzer 3 and the air-trap chamber 5 and measures the hydraulic pressure of the blood flowing through the venous blood circuit 2, thereby measuring the venous pressure of the patient during the blood purification treatment in a time-course manner.

The venous-pressure-measuring unit P according to the present embodiment includes, for example, a chamber portion connected to the venous blood circuit 2, and a sensor or the like that measures the hydraulic pressure in the chamber portion. The chamber portion is filled with the priming solution before the blood purification treatment and with the blood during the blood purification treatment. That is, no air layer is formed in the chamber portion. Thus, the hydraulic pressure of the liquid (blood) flowing through the venous-pressure-measuring unit P is directly measured with the sensor, and the venous pressure of the patient during the blood purification treatment is monitored in a time-course manner.

Specifically, as illustrated in FIG. 4(a), the venous-pressure-measuring unit P according to the present embodiment includes a chamber portion m1 connected to the venous blood circuit 2, and a membrane m2 provided in the chamber portion m1 and that does not allow liquid to permeate therethrough. In the chamber portion m1, a liquid-phase part Q1 filled with liquid and a gas-phase part Q2 filled with air is formed. The gas-phase part Q2 is provided with an atmosphere release line Lf, to which a level-adjusting pump 17 formed of a peristaltic pump is attached. As illustrated in part (b) of the drawing, when the level-adjusting pump 17 is activated, air in the gas-phase part Q2 is discharged to the outside, whereby the position of the membrane m2 (the liquid surface) in the chamber portion m1 is adjusted (in the present embodiment, air in the chamber portion m1 is all discharged, so that no air layer is formed).

The electromagnetic valves V1 to V4, each making the above opening and closing motion, open and close the respective flow routes at the respective positions. The opening and closing motion is controlled by the control unit E, which is a microcomputer or the like. In particular, the control unit E according to the present embodiment receives a detection signal generated by the venous bubble-detecting unit 7 and controls the blood pump 4 and the electromagnetic valves V1 to V4, to all of which the control unit E is electrically connected.

The control unit E according to the present embodiment sequentially executes a priming step in which, before the dialysis treatment (before the blood purification treatment), the priming solution supplied into the blood circuit through the priming-solution supply line Ld is discharged through the overflow line Le (the discharge unit) while flow routes in the blood circuit are filled with the priming solution; a normal rotation step in which, after the priming step, the region filled with the priming solution is closed by the electromagnetic valve V1 (the closing unit) and a backflow is generated in the squeezable tube H by normally rotating the rotor 13 of the blood pump 4 until the roller 14 of the blood pump 4 releases the squeezable tube H to generate a backflow; a reverse rotation step in which, after the backflow is generated in the normal rotation step at the release of the squeezable tube H by the roller 14 of the blood pump 4, bubbles in the squeezable tube H are moved by reversely rotating the rotor 13 while disabling the closing by the electromagnetic valve V1 (the closing unit); and a discharge step in which the bubbles moved in the reverse rotation step are discharged through the overflow line Le (the discharge unit).

Now, a control process executed by the control unit E according to the present embodiment will be described with reference to the flow chart illustrated in FIG. 10.

Before the blood purification treatment, as illustrated in FIGS. 5 and 6, the dialyzer 3 is set with the blood inlet 3a thereof being oriented upward (and is fixed with a fixing member, not illustrated). Furthermore, the connector c and the connector d are connected to each other, whereby the respective flow routes are made to communicate with each other. Then, the priming step (including an overflow step S1 and a liquid-delivering step S2) is executed. In the priming step, the priming solution supplied through the priming-solution supply line Ld is discharged through the overflow line Le (the discharge unit) while flow routes in the blood circuit are filled with the priming solution. In the present embodiment, the overflow step S1 (FIG. 5) and the liquid-delivering step S2 (FIG. 6) are executed repeatedly.

In the overflow step S1, as illustrated in FIG. 5, the blood pump 4 is stopped with the electromagnetic valves (V1 to V4) being open, whereby the priming solution (the dialysate) supplied through the priming-solution supply line Ld is caused to flow into the air-trap chamber 5, and the priming solution overflowing from the air-trap chamber 5 is discharged to the outside through the overflow line Le. Thus, the priming solution (the dialysate) supplied through the priming-solution supply line Ld fills a flow route extending from the connection between the arterial blood circuit 1 and the priming-solution supply line Ld through the connection between the distal end of the arterial blood circuit 1 and the distal end of the venous blood circuit 2 to the air-trap chamber 5, and also fills the air-trap chamber 5.

When a predetermined time elapses after the overflow step S1 is started, the liquid-delivering step S2 is executed. In the liquid-delivering step S2, as illustrated in FIG. 6, the blood pump 4 is rotated reversely (rotated in the direction β indicated in FIG. 6) with the electromagnetic valves (V1 and V2) being open and the electromagnetic valves (V3 and V4) being closed, whereby the priming solution (the dialysate) supplied in the overflow step S1 is delivered (caused to circulate) through the blood circuit. Thus, the priming solution flows through the blood-side flow routes in the dialyzer 3 from the lower side toward the upper side. Therefore, bubbles smoothly move upward and are removed.

After the above liquid-delivering step S2, whether any bubbles have been detected by the venous bubble-detecting unit 7 is checked (S3). If it is judged that bubbles have been detected, the overflow step S1 is executed again. After the overflow step S1 is continued for a predetermined time, the liquid-delivering step S2 is executed. Then, whether any bubbles have been detected is checked again in S3. As the overflow step S1 and the liquid-delivering step S2 are repeatedly executed until no bubbles are detected by the venous bubble-detecting unit 7, the blood circuit and the air-trap chamber 5 become fully filled with the priming solution.

If it is judged that no bubbles are detected by the venous bubble-detecting unit 7 in S3 and the priming step (including the overflow step S1 and the liquid-delivering step S2) is thus ended, the flow routes in the arterial blood circuit 1 and in the venous blood circuit 2 and the blood flow routes in the dialyzer 3 become fully filled with the priming solution (a filled state), and the air-trap chamber 5 and the chamber portion of the venous-pressure-measuring unit P also become fully filled with the priming solution (a state where no air layer is formed).

When the priming step is ended as above, the normal rotation step S4 is executed. In the normal rotation step S4, as illustrated in FIG. 7, the blood pump 4 is rotated normally (rotated in the direction α indicated in FIG. 7) with the electromagnetic valves (V1, V3, and V4) being closed and the electromagnetic valve V2 being open, whereby a negative pressure is generated in the squeezable tube H. Furthermore, the rotor 13 of the blood pump 4 is rotated normally until the roller 14 of the blood pump 4 releases the squeezable tube H to generate a backflow in the squeezable tube H. In this case, the closing unit is formed of the electromagnetic valve V1 (the closing unit).

Specifically, when the blood pump 4 is rotated normally (rotated in the direction α indicated in FIG. 7) with the electromagnetic valves (V1, V3, V4) being closed, a negative pressure can be generated not only in a flow route in the arterial blood circuit 1 between the blood pump 4 and the electromagnetic valve V1 but also, as illustrated in FIG. 11, in part of the squeezable tube H (a flow route Ha before a region being squeezed by the roller 14). Note that reference character Hb in the drawing denotes a flow route in the squeezable tube H that is free from the negative pressure (a flow route in a region not being squeezed by the roller 14). As illustrated in FIG. 12, at the instant that the roller 14 of the blood pump 4 has released the squeezable tube H, a backflow occurs with the restoring force exerted by the squeezable tube H. The backflow causes microbubbles to move in the same direction (a direction indicated by reference character γ in FIG. 12).

In S5, when the reaching of the roller 14 to a predetermined position where the roller 14 releases the squeezable tube H is detected by the position-detecting unit S, the process proceeds to a reverse rotation step S6. In the reverse rotation step S6, after the roller 14 of the blood pump 4 has released the squeezable tube H to generate a backflow in the normal rotation step S4, the rotor 13 is rotated reversely while the closing by the closing unit (the electromagnetic valve V1) is disabled. Thus, not only microbubbles remaining in the squeezable tube H but also microbubbles detached from flow routes in the blood circuit and in the blood purification unit are moved.

More specifically, in the reverse rotation step S6, as illustrated in FIG. 8, the blood pump 4 is rotated reversely with the electromagnetic valves (V1 and v2) being open and the electromagnetic valves (V3 and V4) being closed, whereby not only microbubbles remaining in the squeezable tube H but also microbubbles detached from the flow routes in the blood circuit and in the blood purification unit are moved to the air-trap chamber 5. In the reverse rotation step S6, the closing by the electromagnetic valve V1 is disabled (that is, the electromagnetic valve V1 is opened). Therefore, as illustrated in FIG. 13, the squeezable tube H is squeezed by the roller 14 while the negative pressure is removed.

After the reverse rotation step S6, the discharge step S7 is executed. In the discharge step S7, the bubbles moved in the reverse rotation step S6 are discharged through the overflow line Le (the discharge unit). As illustrated in FIG. 9, the blood pump 4 is stopped with the electromagnetic valves (V1 to V4) being open, whereby the bubbles having flowed into the air-trap chamber 5 in the reverse rotation step S6 can be discharged to the outside through the overflow line Le. Thus, through the reverse rotation step S6 and the discharge step S7, the microbubbles moved along with the backflow generated in the normal rotation step S4 can be discharged to the outside.

According to the present embodiment, after the priming step (including the overflow step S1 and the liquid-delivering step S2), the normal rotation step is executed in which the region filled with the priming solution is closed by the electromagnetic valve V1 (the closing unit) and the rotor 13 of the blood pump 4 is rotated normally until the roller 14 of the blood pump 4 releases the squeezable tube H to generate a backflow. Therefore, with the use of the backflow generated at the instant that the roller 14 of the blood pump 4 has released the squeezable tube H, not only microbubbles remaining in the squeezable tube H after the priming step but also microbubbles detached from the flow routes in the blood circuit and in the blood purification unit can be discharged smoothly and assuredly.

According to the above embodiment, the blood purification apparatus includes the detecting unit (the position-detecting unit S) that detects the position where the roller 14 of the blood pump 4 releases the squeezable tube H. Therefore, immediately after the backflow is generated, the normal rotation step can be ended for the subsequent reverse rotation step. Hence, bubbles moved along with the backflow are prevented from moving backward and can be discharged through the discharge unit (the overflow line Le). In particular, the detecting unit according to the present embodiment is formed of the position-detecting unit S that detects the position of the roller 14. Therefore, the position where the roller 14 of the blood pump 4 releases the squeezable tube H to generate a backflow can be precisely detected by the position-detecting unit S.

According to the present embodiment, the venous blood circuit 2 is provided with the air-trap chamber 5 connected thereto. Furthermore, the discharge unit for discharging bubbles is formed of the overflow line Le extending from the top of the air-trap chamber 5. Therefore, when the priming step is executed with the distal end of the arterial blood circuit 1 and the distal end of the venous blood circuit 2 being connected to each other, not only microbubbles remaining in the squeezable tube H but also microbubbles detached from the flow routes in the blood circuit and in the blood purification unit can be discharged in a good manner through the overflow line Le.

Now, a second embodiment of the present invention will be described.

As with the case of the first embodiment, a blood purification apparatus according to the second embodiment is a dialysis apparatus intended for dialysis treatment and basically includes, as illustrated in FIG. 14, a blood circuit formed of an arterial blood circuit 1 and a venous blood circuit 2, a dialyzer 3 (a blood purification unit) connected to a proximal end of the arterial blood circuit 1 and to a proximal end of the venous blood circuit 2 and that purifies blood flowing through the blood circuit, an air-trap chamber 5 connected to the venous blood circuit 2, a priming-solution supply line Ld connected to the arterial blood circuit 1 and through which a priming solution is supplied into the blood circuit, a closing unit (in the present embodiment, an electromagnetic valve V1) that closes a region filled with the priming solution in the blood circuit and thus generates a negative pressure in a squeezable tube H when a rotor 13 of a blood pump 4 is rotated normally, and a control unit E that controls the blood pump 4 and the closing unit (the electromagnetic valve V1).

The discharge unit (the discharge unit that allows the priming solution supplied into the blood circuit through the priming-solution supply line Ld to be discharged to the outside) according to the present embodiment is formed of a distal end of the arterial blood circuit 1 or a distal end of the venous blood circuit 2. The present embodiment does not employ the overflow line Le, which extends from the air-trap chamber 5 according to the first embodiment. Elements that are the same as those described in the first embodiment are denoted by corresponding ones of the reference numerals, and detailed description of those elements is omitted.

Now, a control process executed by the control unit E according to the present embodiment will be described with reference to the flow chart illustrated in FIG. 18.

Before the blood purification treatment, as illustrated in FIGS. 14 and 15, the dialyzer 3 is set with the blood inlet 3a thereof being oriented upward (and is fixed with a fixing member, not illustrated). Furthermore, the connector c and the connector d are each freed (the connectors are not connected to each other). Then, the priming step (including an arterial priming step S1 and a venous priming step S2) is executed. In the priming step, the priming solution supplied through the priming-solution supply line Ld is discharged from the distal ends (the discharge unit) of the arterial blood circuit 1 and the venous blood circuit 2 while flow routes in the blood circuit are filled with the priming solution. In the present embodiment, the arterial priming step S1 (FIG. 14) and the venous priming step S2 (FIG. 15) are executed.

In the arterial priming step S1, as illustrated in FIG. 14, the blood pump 4 is stopped with the electromagnetic valves (V1, V2, and V4) being open, whereby the priming solution (the dialysate) supplied through the priming-solution supply line Ld is caused to flow to the distal end of the arterial blood circuit 1 and is discharged from the distal end to the outside. Thus, the priming solution (the dialysate) supplied through the priming-solution supply line Ld fills a flow route extending from the connection between the arterial blood circuit 1 and the priming-solution supply line Ld to the distal end of the arterial blood circuit 1.

When a predetermined time elapses after the arterial priming step S1 is started, the venous priming step S2 is executed. In the venous priming step S2, as illustrated in FIG. 15, the blood pump 4 is rotated normally with the electromagnetic valves (V2 and V4) being open and the electromagnetic valve V1 being closed, whereby the priming solution (the dialysate) supplied through the priming-solution supply line Ld is caused to flow to the distal end of the venous blood circuit 2 and is discharged from the distal end to the outside. Thus, the priming solution (the dialysate) supplied through the priming-solution supply line Ld fills a flow route extending from the connection between the arterial blood circuit 1 and the priming-solution supply line Ld through the blood flow routes in the dialyzer 3 to the distal end of the venous blood circuit 2.

Subsequently, when a predetermined time elapses after the venous priming step S2 is started and the priming step is thus ended, the flow routes in the arterial blood circuit 1 and in the venous blood circuit 2 and the blood flow routes in the dialyzer 3 become fully filled with the priming solution (a filled state), and the air-trap chamber 5 and the chamber portion of the venous-pressure-measuring unit P also become fully filled with the priming solution (a state where no air layer is formed).

When the priming step is ended as above, the normal rotation step S3 is executed. In the normal rotation step S3, as illustrated in FIG. 16, the blood pump 4 is rotated normally with the electromagnetic valves (V1, V2, and V4) being closed, whereby a negative pressure is generated in the squeezable tube H, and the rotor 13 of the blood pump 4 is rotated normally until the roller 14 of the blood pump 4 releases the squeezable tube H to generate a backflow in the squeezable tube H. In this case, the closing unit is formed of the electromagnetic valve V1 (the closing unit).

Specifically, when the blood pump 4 is rotated normally with the electromagnetic valves (V1, V2, V4) being closed, a negative pressure can be generated not only in a flow route in the arterial blood circuit 1 between the blood pump 4 and the electromagnetic valve V1 but also, as illustrated in FIG. 11, in part of the squeezable tube H (the flow route Ha before the region being squeezed by the roller 14). Note that reference character Hb in the drawing denotes a flow route in the squeezable tube H that is free from the negative pressure (a flow route in a region not being squeezed by the roller 14). As illustrated in FIG. 12, at the instant that the roller 14 of the blood pump 4 has released the squeezable tube H, a backflow occurs with the restoring force exerted by the squeezable tube H. The backflow causes microbubbles to move in the same direction (a direction indicated by reference character γ in FIG. 12).

In S4, when the reaching of the roller 14 to a predetermined position where the roller 14 releases the squeezable tube H is detected by the position-detecting unit S, the process proceeds to a reverse rotation step and a discharge step S5. In the reverse rotation step and the discharge step S5, after the roller 14 of the blood pump 4 has released the squeezable tube H to generate a backflow in the normal rotation step S4, the rotor 13 is rotated reversely while the closing by the closing unit (the electromagnetic valve V1) is disabled. Thus, not only microbubbles remaining in the squeezable tube H but also microbubbles detached from flow routes in the blood circuit and in the blood purification unit are moved and discharged through the distal end (the discharge unit) of the arterial blood circuit 1.

More specifically, in the reverse rotation step and the discharge step S5, as illustrated in FIG. 17, the blood pump 4 is rotated reversely with the electromagnetic valves (V1 and V2) being open and the electromagnetic valve V4 being closed, whereby not only the squeezable tube H but also microbubbles detached from the blood circuit and the dialyzer 3 are moved along with the backflow and are discharged to the outside through the distal end of the arterial blood circuit 1 and the distal end of the venous blood circuit 2 (the discharge unit). In the reverse rotation step and the discharge step S5, the closing by the electromagnetic valve V1 is disabled (that is, the electromagnetic valve V1 is opened). Therefore, as illustrated in FIG. 13, the squeezable tube H is squeezed by the roller 14 while the negative pressure is removed. Thus, through the reverse rotation step and the discharge step S5, the microbubbles moved along with the backflow generated in the normal rotation step S3 (the microbubbles remaining in the squeezable tube H and the microbubbles detached from the flow routes in the blood circuit and in the blood purification unit) can be discharged to the outside.

According to the present embodiment, after the priming step (including the arterial priming step S1 and the venous priming step S2), the region filled with the priming solution is closed by the electromagnetic valve V1 (the closing unit) and the rotor 13 of the blood pump 4 is rotated normally until the roller 14 of the blood pump 4 releases the squeezable tube H to generate a backflow. Therefore, with the use of the backflow generated at the instant that the roller 14 of the blood pump 4 has released the squeezable tube H, not only microbubbles remaining in the squeezable tube H after the priming step but also microbubbles detached from the flow routes in the blood circuit and in the blood purification unit can be discharged smoothly and assuredly.

According to the above embodiment, the blood purification apparatus includes the detecting unit (the position-detecting unit S) that detects the position where the roller 14 of the blood pump 4 releases the squeezable tube H. Therefore, immediately after the backflow is generated, the normal rotation step can be ended for the subsequent reverse rotation step. Hence, bubbles moved along with the backflow are prevented from moving backward and can be discharged through the discharge unit (the overflow line Le). In particular, the detecting unit according to the present embodiment is formed of the position-detecting unit S that detects the position of the roller 14. Therefore, the position where the roller 14 of the blood pump 4 releases the squeezable tube H to generate a backflow can be precisely detected by the position-detecting unit S.

According to the present embodiment, the discharge unit for discharging bubbles is formed of the distal end of the arterial blood circuit 1 (or may be the distal end of the venous blood circuit 2). Therefore, when the priming step is executed without connecting the distal end of the arterial blood circuit 1 and the distal end of the venous blood circuit 2 to each other, not only microbubbles remaining in the squeezable tube H but also microbubbles detached from the flow routes in the blood circuit and in the blood purification unit can be discharged in a good manner from the distal end of the arterial blood circuit 1 (or the distal end of the venous blood circuit).

While some embodiments have been described above, the present invention is not limited thereto. For example, as illustrated in FIG. 19, the position-detecting unit S may be omitted. Instead, the venous-pressure-measuring unit P may be used as the detecting unit that detects the position where the roller 14 of the blood pump 4 releases the squeezable tube H. That is, since the venous-pressure-measuring unit P detects the pressure in the blood circuit that changes with the normal rotation of the roller 14 (changes with pulsation), the venous-pressure-measuring unit P can detect the position where the roller 14 of the blood pump 4 releases the squeezable tube H, in accordance with changes in the detected pressure. In such a case, the position where the roller 14 of the blood pump 4 releases the squeezable tube H to generate a backflow can be detected with the use of the venous-pressure-measuring unit P, which is necessary for blood purification treatment.

The priming step may be any other type of step, as long as the priming solution supplied through the priming-solution supply line Ld is discharged through the discharge unit (such as the overflow line Le, or the distal end of the arterial blood circuit 1 or the venous blood circuit 2) while a flow route in the blood circuit is filled with the priming solution.

The priming-solution supply line Ld according to the present embodiment is connected at one end thereof to the dialysate introduction line La and allows the dialysate as the priming solution to be supplied to the blood circuit when the electromagnetic valve V4 is open. Alternatively, for example, one end of the priming-solution supply line Ld may be connected to a storage bag storing a physiological saline solution so that the physiological saline solution can be supplied as the priming solution to the blood circuit. As another alternative, the priming-solution supply line Ld may be omitted. Instead, for example, the dialysate (the priming solution) in the dialysate introduction line La may be filtered (back-filtered) through the purification membranes (in the present embodiment, the hollow fiber membranes) in the dialyzer 3 before being supplied to the blood circuit (the arterial blood circuit 1 and the venous blood circuit 2).

In addition, the priming solution may be another liquid different from dialysate or a physiological saline solution. While the above embodiments are each applied to a dialysis apparatus intended for dialysis treatment, the present invention may also be applied to another apparatus (such as a blood purification apparatus or a plasma adsorption apparatus intended for hemodiafiltration, hemofiltration, or AFBF) that purifies a patient's blood while causing the blood to extracorporeally circulate.

The present invention is applicable to any blood purification apparatus and any method of discharging bubbles therefrom that are of any other type or for any other use, as long as the following are executed: a priming step in which a priming solution supplied is discharged through a discharge unit while a flow route in a blood circuit is filled with the priming solution; a normal rotation step in which, after the priming step, the region filled with the priming solution is closed by a closing unit, and a rotor of a blood pump is rotated normally until the roller of the blood pump releases a squeezable tube to generate a backflow; a reverse rotation step in which, after the backflow is generated in the normal rotation step at the release of the squeezable tube by the roller of the blood pump, bubbles are moved by reversely rotating the rotor while disabling the closing by the closing unit; and a discharge step in which the bubbles moved in the reverse rotation step are discharged through the discharge unit.

Note that the region filled with the priming solution refers to the entirety or part of a portion of the blood circuit that is filled with the priming solution.

REFERENCE SIGN LIST

1 arterial blood circuit
2 venous blood circuit
3 dialyzer (blood purification unit)
4 blood pump
5 air-trap chamber
6 arterial bubble-detecting unit
7 venous bubble-detecting unit
8, 9 blood identifier
10 duplex pump
11 ultrafiltration pump
12 stator
12*a* fitting recess
13 rotor
14 roller (squeezing unit)
15 guide pin
16 holding portion
17 level-adjusting pump
P venous-pressure-measuring unit
S position-detecting unit
H squeezable tube
E control unit
La dialysate introduction line
Lb dialysate drain line
Lc bypass line
Ld priming-solution supply line
Le overflow line
Lf atmosphere release line

The invention claimed is:

1. A blood purification apparatus comprising:
a blood circuit including an arterial blood circuit and a venous blood circuit and allowing a patient's blood to extracorporeally circulate from a distal end of the arterial blood circuit to a distal end of the venous blood circuit;
a blood purification unit connected to a proximal end of the arterial blood circuit and to a proximal end of the venous blood circuit and that purifies the blood flowing through the blood circuit;
a squeezable tube connected to the arterial blood circuit;
a blood pump formed of a peristaltic pump that delivers liquid by squeezing, the squeezable tube between a roller and a stator while a rotor is driven to rotate relative to an inner peripheral wall of the stator, the blood pump delivering the liquid from the distal end of the arterial blood circuit toward the blood purification unit when the rotor is rotated normally such that the roller moves in a lengthwise direction of the squeezable tube, the blood pump delivering the liquid from the blood purification unit toward the distal end of the arterial blood circuit when the rotor is rotated reversely such that the roller moves in the lengthwise direction of the squeezable tube;

a discharge unit through which a priming solution supplied into the blood circuit is discharged to an outside of the blood circuit;

a closing unit that generates a negative pressure in the squeezable tube, when the rotor is rotated normally, by closing a region of the blood pump that is filled with the priming solution;

a detecting unit that detects a position where the roller of the blood pump releases the squeezable tube; and a control unit that controls the blood pump and the closing unit, wherein the control unit executes a priming step in which the priming solution supplied into the blood circuit is discharged through the discharge unit while a flow route in the blood circuit is filled with the priming solution;

a normal rotation step in which, after the priming step, the region filled with the priming solution is closed by the closing unit, and the rotor of the blood pump is rotated normally until the roller of the blood pump releases the squeezable tube to generate a backflow;

a reverse rotation step in which, after the backflow is generated in the normal rotation step when releasing the squeezable tube by the roller of the blood pump, bubbles are moved by reversely rotating the rotor while disabling the closing by the closing unit, wherein the reverse rotation step is triggered by the detecting unit detecting the position where the roller releases the squeezable tube; and a discharge step in which the bubbles moved in the reverse rotation step are discharged through the discharge unit.

2. The blood purification apparatus according to claim 1, wherein the detecting unit is formed of a position-detecting unit that detects a position of the roller.

3. The blood purification apparatus according to claim 1, wherein the detecting unit is formed of a pressure-detecting unit that detects a pressure in the blood circuit, the pressure changing when the rotor is rotated normally.

4. The blood purification apparatus according to claim 1, wherein the venous blood circuit is provided with an air-trap chamber connected thereto, and wherein the discharge unit is formed of an overflow line extending from a top of the air-trap chamber.

5. The blood purification apparatus according to claim 1, wherein the discharge unit is formed of the distal end of the arterial blood circuit or the distal end of the venous blood circuit.

6. The blood purification apparatus according to claim 3, wherein the venous blood circuit is provided with an air-trap chamber connected thereto, and wherein the discharge unit is formed of an overflow line extending from a top of the air-trap chamber.

7. The blood purification apparatus according to claim 3, wherein the discharge unit is formed of the distal end of the arterial blood circuit or the distal end of the venous blood circuit.

8. The blood purification apparatus according to claim 1, further comprising:

a venous-pressure-measuring unit comprising a chamber portion.

9. The blood purification apparatus according to claim 8, wherein the chamber portion comprises a membrane that separates a liquid-phase part filled with the liquid and a gas-phase part filled with air.

10. The blood purification apparatus according to claim 1, wherein the detecting unit detects a position of the roller by detecting an angle of rotation of the rotor.

11. A method of discharging bubbles from a blood purification apparatus, the apparatus including a blood circuit including an arterial blood circuit and a venous blood circuit and allowing a patient's blood to extracorporeally circulate from a distal end of the arterial blood circuit to a distal end of the venous blood circuit;

a blood purification unit connected to a proximal end of the arterial blood circuit and to a proximal end of the venous blood circuit and that purifies the blood flowing through the blood circuit;

a squeezable tube connected to the arterial blood circuit;

a blood pump formed of a peristaltic pump that delivers liquid by squeezing the squeezable tube between a roller and a stator while a rotor is driven to rotate relative to an inner peripheral wall of the stator, the blood pump delivering the liquid from the distal end of the arterial blood circuit toward the blood purification unit when the rotor is rotated normally such that the roller moves in a lengthwise direction of the squeezable tube, the blood pump delivering the liquid from the blood purification unit toward the distal end of the arterial blood circuit when the rotor is rotated reversely such that the roller moves in the lengthwise direction of the squeezable tube;

a discharge unit through which a priming solution supplied into the blood circuit is discharged to an outside of the blood circuit;

a detecting unit that detects a position where the roller of the blood pump releases the squeezable tube; and a closing unit that generates a negative pressure in the squeezable tube, when the rotor is rotated normally, by closing a region of the blood pump that is filled with the priming solution, wherein the method comprising:

a priming step in which the priming solution supplied into the blood circuit is discharged through the discharge unit while a flow route in the blood circuit is filled with the priming solution;

a normal rotation step in which, after the priming step, the region filled with the priming solution is closed by the closing unit, and the rotor of the blood pump is rotated normally until the roller of the blood pump releases the squeezable tube to generate a backflow;

a reverse rotation step in which, after the backflow is generated in the normal rotation step when releasing the squeezable tube by the roller of the blood pump, the bubbles are moved by reversely rotating the rotor while disabling the closing by the closing unit, wherein the reverse rotation step is triggered by the detecting unit detecting the position where the roller releases the squeezable tube; and a discharge step in which the bubbles moved in the reverse rotation step are discharged through the discharge unit.

12. The method of discharging the bubbles from the blood purification apparatus according to claim 11, wherein the detecting unit is formed of a position-detecting unit that detects a position of the roller.

13. The method of discharging the bubbles from the blood purification apparatus according to claim 11, wherein the detecting unit is formed of a pressure-detecting unit that detects a pressure in the blood circuit, the pressure changing when the rotor is rotated normally.

14. The method of discharging the bubbles from the blood purification apparatus according to claim 11, wherein the venous blood circuit is provided with an air-trap chamber connected thereto, and wherein the discharge unit is formed of an overflow line extending from a top of the air-trap chamber.

15. The method of discharging the bubbles from the blood purification apparatus according to claim 13, wherein the discharge unit is formed of the distal end of the arterial blood circuit or the distal end of the venous blood circuit.

16. The method of discharging the bubbles from the blood purification apparatus according to claim 13, wherein the venous blood circuit is provided with an air-trap chamber connected thereto, and wherein the discharge unit is formed of an overflow line extending from a top of the air-trap chamber.

17. The method of discharging the bubbles from the blood purification apparatus according to claim 11, further comprising:
 a venous-pressure-measuring unit comprising a chamber portion.

18. The method of discharging the bubbles from the blood purification apparatus according to claim 17, wherein the chamber portion comprises a membrane that separates a liquid-phase part filled with the liquid and a gas-phase part filled with air.

19. The method of discharging the bubbles from the blood purification apparatus according to claim 11, wherein the detecting unit detects a position of the roller by detecting an angle of rotation of the rotor.

* * * * *